United States Patent [19]
Cohenford et al.

[11] Patent Number: 6,146,897
[45] Date of Patent: Nov. 14, 2000

[54] METHOD FOR THE DETECTION OF CELLULAR ABNORMALITIES USING FOURIER TRANSFORM INFRARED SPECTROSCOPY

[75] Inventors: Menashi A. Cohenford, West Warwick, R.I.; Prashant S. Bhandare, Arlington, Mass.; Basil Rigas, White Plains, N.Y.

[73] Assignee: Bio-Rad Laboratories, Hercules, Calif.

[21] Appl. No.: 08/851,776

[22] Filed: May 6, 1997

Related U.S. Application Data

[63] Continuation-in-part of application No. 08/747,375, Nov. 12, 1996, Pat. No. 5,976,885, which is a continuation-in-part of application No. 08/558,130, Nov. 13, 1995, Pat. No. 6,031,232.

[51] Int. Cl.$^7$ .................................................. G01N 33/48
[52] U.S. Cl. .............................. 436/63; 436/64; 436/171; 600/473; 600/475; 250/338.1; 250/339.09; 250/339.12; 250/341.1
[58] Field of Search ................................ 436/63, 64, 171, 436/172; 600/473, 475, 476–478; 250/338.1, 339.01, 339.09, 339.12, 341.1, 341.8, 461.2

[56] References Cited

U.S. PATENT DOCUMENTS

| | | | |
|---|---|---|---|
| 5,036,853 | 8/1991 | Jeffcoat et al. | 600/342 |
| 5,038,039 | 8/1991 | Wong et al. | 250/339 |
| 5,168,162 | 12/1992 | Oong et al. | 250/339.12 |
| 5,197,470 | 3/1993 | Helfer et al. | 600/342 |
| 5,435,309 | 7/1995 | Thomas et al. | 600/310 |
| 5,539,207 | 7/1996 | Wong | 250/339.08 |
| 5,596,992 | 1/1997 | Haaland et al. | 600/473 |
| 5,608,519 | 3/1997 | Gourley et al. | 356/318 |
| 5,733,739 | 3/1998 | Zakim et al. | 435/29 |

OTHER PUBLICATIONS

Dong et al. *Biochemical & Biophysical Research Communications*, vol. 156, pp. 752–756. (Abstract), Oct. 31, 1988.
Zhengfang Ge, et al., Screening Pap Smears with Near–Infrared Spectroscopy, 1995, vol. 49, No. 4, Society for Applied Spectroscopy, pp. 432–436.

*Primary Examiner*—Maureen M. Wallenhorst
*Attorney, Agent, or Firm*—Townsend and Townsend and Crew LLP

[57] ABSTRACT

This invention teaches a method to identify cellular abnormalities which are associated with disease states. The method utilizes infrared (IR) spectra of cell samples which are dried on an infrared-transparent matrix and scanned at the frequency range from 3000–950 cm$^{-1}$. The identification of samples is based on establishing a reference using a representative set of spectra of normal and/or diseased specimens. During the reference assembly process, multivariate techniques such as Principal Component Analysis (PCA) and/or Partial Least Squares (PLS) are used. PCA and PLS reduce the data based on maximum variations between the spectra, and generate clusters in a multidimensional space representing the different populations. The utilization of Mahalinobis distances, or linear regression (e.g., Principle Component Regression on the reduced data from PCA) form the basis for the discrimination. In one embodiment, the invention is a method to distinguish premalignant and malignant stages of cervical cancer from normal cervical cells. This method is simple to use and achieves statistically reliable distinction between the following groups of cervical smears: normal (individuals with no prior history of dysplasia), dysplasia and malignant samples. Further, this invention discloses a method to obtain the IR spectrum of individual cervical cells fixed on an infrared-transparent matrix and to use the spectra of the individual cells in the method described above. In another aspect, the invention is a method for using vibrational spectroscopic imaging to distinguish between normal and diseased cells. In another aspect, the invention is a method to identify women at a high risk for developing cervical dysplasia.

40 Claims, 15 Drawing Sheets

| RANGE | 33%-52% | 16%-71% | 1%-22% | 4%-27% |
| --- | --- | --- | --- | --- |
| PREDICTED SCORES, MEAN ± SEM BASED ON TOTAL OF 4 SMEARS | 0.446±.02 | 0.445±.08 | 0.772±0.04 | 0.741±0.065 |

N = NORMAL SMEARS
N-D = NORMAL DYSPLASIA SMEARS
D = DYSPLASIA SMEARS
C = MALIGNANT SMEARS

| RANGE | 98%-100% | 45%-71% | 55%-79% | 1%-38% |
| PREDICTED SCORES, MEAN±SEM | 0.0016±0.047 | 0.422±0.056 | 0.329±0.046 | 0.783±0.09 |
| BASED ON TOTAL OF 4 SMEARS | * | * | * | |

N = NORMAL SMEARS
N-D = NORMAL DYSPLASIA SMEARS
D = DYSPLASIA SMEARS
C = MALIGNANT SMEARS
* = OVERLAP OF ONE OR MORE THAN ONE DATA POINTS

METHOD FOR THE DETECTION OF CELLULAR ABNORMALITIES USING FOURIER TRANSFORM INFRARED SPECTROSCOPY

CROSS-REFERENCE TO RELATED APPLICATIONS

This application is a Continuation-in-Part of U.S. Ser. No. 08/747,375, filed Nov. 12, 1996, now U.S. Pat. No. 5,976,885 issued on Nov. 2, 1999 which is a Continuation-in-Part of U.S. Ser. No. 08/558,130, filed Nov. 13, 1995, now U.S. Pat. No. 6,031,232 issued on Feb. 29, 2000 the disclosures of each being incorporated herein by reference.

BACKGROUND OF THE INVENTION

The detection of premalignant and malignant cells by the Papanicolaou smear (Pap smear) has greatly reduced the high mortality rate due to cervical cancer. Nevertheless, the Pap screening process is labor intensive and has remained essentially unchanged since it was first described by Papanicolaou almost 50 years ago. To perform the test, cells are exfoliated from a patient's cervix by scraping using a spatula or brush. The scraping is then smeared on a slide, and the slide is stained and microscopically examined. The microscopic examination is a tedious process, and requires a cytotechnologist to visually scrutinize all the fields within a slide to detect the often few aberrant cells in a specimen. Consequently, the detection of abnormal specimens depends on the level of a cytotechnologist's experience and workload, and also on the quality of the smear preparation.

A recent critical evaluation of the Pap smear reported that the error rates associated with the current technique can be startlingly high. For example, the reported false negative rate (sensitivity) ranges from 6% to 55% (see, Shingleton, H. M., et al., *CA Cancer J. Clin.*, 45:305–320 (1995)).

As a result of these concerns, attempts have been made to automate the Pap screening process and to standardize the staining procedure. Certain of the available automated systems have been designed to improve the diagnostic yield of the Pap smear by minimizing the content of blood, mucus and other non-diagnostic debris in the examined cervical scrapings. In spite of these changes and the resulting simplification of the sample, the diagnosis of Pap smears continues to be heavily influenced by subjective bias. Thus, efforts are currently being directed towards developing alternative means of diagnosing Pap smears which are based on objective criteria such as chemical or morphological changes in cervical cells.

A number of methods have been explored to detect cytological anomalies, including those using molecular and immunological techniques. One impetus behind the development of new molecular and immunological methods is the detection of the human papilloma virus (HPV). Certain subtypes of HPV have been linked to a high incidence of abnormal lesions, and are implicated in the etiology of cervical cancer. Although these techniques are specific and detect cervical specimens at high risk, they are currently cost prohibitive and too labor intensive.

Recently, differences have been reported in the Fourier Transform Infrared (FT-IR) spectra of 156 cervical samples, of which by cytological screening, 136 were normal, 12 had cancer, and 8 had dysplasia (see, Wong et al., *Proc. Natl. Acad. Sci. USA*, 87:8140–8145 (1991)). This study relied on features of the mid-IR region (3000–950 $cm^{-1}$) to discriminate between the samples. The spectra of normal samples exhibited a prominent peak at 1025 $cm^{-1}$ which appears to be due to glycogen, and other less pronounced bands at 1047 $cm^{-1}$, 1082 $cm^{-1}$, 1155 $cm^{-1}$ and 1244 $cm^{-1}$. The spectra of specimens diagnosed with cancer exhibited significant changes in the intensity of the bands at 1025 $cm^{-1}$ and 1047 $cm^{-1}$, and demonstrated a peak at 970 $cm^{-1}$ which was absent in normal specimens. Samples with cancer also showed a significant shift in the normally appearing peaks at 1082 $cm^{-1}$, 1155 $cm^{-1}$ and 1244 $cm^{-1}$. The cervical specimens diagnosed cytologically as dysplasia exhibited spectra intermediate in appearance between normal and malignant. Based on these observations, Wong et al. concluded that FT-IR spectroscopy may provide a reliable and cost effective alternative for screening cervical specimens.

The FT-IR spectroscopic studies of Wong, et al. (1991) focused primarily on the differences between normal and malignant samples, and utilized only a few dysplastic specimens. More importantly, discrimination between specimens was achieved by inspection of spectra, and by visually detecting overt changes in peak intensity ratios at specified frequencies. Visual inspection as a basis of discrimination is not an ideal method of analysis. This approach lends itself to subjective bias and is frequently insensitive to small variations between spectra. In the case of malignant specimens, the spectral patterns are markedly altered compared to those of normal samples. However, the spectra of a great majority of specimens with low grade dysplasia (e.g. CIN I-cervical intraepithelial neoplasia) appear similar to spectra from normal samples and are difficult to distinguish. As a result, visual inspection is unreliable and unsuited for the analysis of cervical specimens.

The method of selecting peak intensity ratios to discriminate between spectra has its problems as well. This technique identifies general shapes and patterns, and like the previous approach can lack acuity in the detection of subtle differences between spectra. Other disadvantages of this method include its inability to model for interferences that can be caused by nondiagnostic debris, and/or errors that can result from sample preparation and handling techniques. Aside from the latter, this method can also fail to adequately model for baseline shifts, spectral fringes, batch to batch variations in samples and/or to account for the nonlinearities that can arise from spectroscopic instrumentation and refractive dispersion of infrared light.

More recently, others have reported a greater diversity in the spectra of specimens with dysplasia than previously reported by Wong et al. (see Morris, et al., *Gynecologic Oncology* 56:245–249 (1995)). Out of the 25 specimens that were evaluated, the spectra of 9/13 specimens with low grade dysplasia (CIN I) appeared essentially similar to the spectra of normal specimens. However, as dysplasia progressed from low to high (CIN I to CIN III), the magnitude of spectral differences between normal and dysplastic samples intensified. This difference was most apparent in specimens with high grade dysplasia (CIN III) which exhibited a characteristic peak at 972 $cm^{-1}$, and changes in intensity of bands at 1026 $cm^{-1}$ (decreased), 1081 $cm^{-1}$ (increased and shifted to higher frequency), 1156 cm$^{-1}$ (decreased and flattened), and 1240 cm$^{-1}$ (increased).

Even more recent studies focusing on the greater diversity in the spectra of specimens with dysplasia (Cohenford et al., *Mikrochemica Acta*, in press), have indicated that the extent of spectral changes could perhaps correlate with different stages of cervical abnormalities. For example, as Morris and co-workers demonstrated (*Gynecologic Oncology*, 56:245–249 (1995)), the spectra of specimens with severe dysplasia (CIN III) had an appearance which was intermediate between those of specimens which were diagnosed normal and those diagnosed as containing malignant cells. Unfortunately, the IR spectra of specimens which displayed mild dysplasia (CIN I) appeared essentially similar to the spectra of normal specimens.

The progression of dysplastic cells to malignant cells is not only well documented, but is also of fundamental importance in early diagnosis and prevention of cancer. As it is important, from a clinical point of view, to distinguish those specimens with dysplastic cells from those with only normal cells, a generally useful method using IR spectroscopy must be capable of this rather fine distinction. Quite surprisingly, the present invention provides such methods.

SUMMARY OF THE INVENTION

The present invention provides methods for the spectroscopic detection of chemical differences between cells in a sample of cells or tissue. The methods provided include single-cell infrared microspectroscopy and infrared spectroscopic imaging. In general, the data acquired by the microspectroscopic or imaging process is analyzed using multivariate analysis. In certain embodiments the detected chemical difference is associated with a disease state, particularly a malignant or premalignant state. In these embodiments, the invention provides a method for the early detection of a malignant or premalignant state. In another aspect, the invention provides a spectroscopic method for distinguishing between cells in a cell sample which are cytologically and chemically "normal" and those cells in a cell sample which appear cytologically normal but which are, in fact, "chemically aberrant." In yet another aspect, the invention provides a spectroscopic method for the identification of women who are at high risk for developing cervical dysplasia.

Throughout the discussion below and in the examples cervical cells are utilized as an exemplary cell type. The exemplary use of cervical cells does not limit or define the scope of the present invention.

Thus, in a first aspect, the invention provides a method for detecting chemical differences between a cell sample and a reference cell sample, utilizing single-cell infrared microspectroscopy, the method comprising:

(a) directing a beam of infrared light at single cells in a cell sample to produce absorption data for each of the single cells;

(b) comparing the absorption data for each of the single cells with infrared absorption spectra acquired from individual cells in at least one reference cell sample to provide comparison data for each of the single cells in the cell sample.

In a second aspect, the invention provides a method for detecting chemical differences between a cell sample and a reference cell sample utilizing single-cell infrared microspectroscopy, the method comprising:

(a) directing a beam of infrared light at single cells in the cell sample to produce absorption data for each of the single cells;

(b) comparing the absorption data for the single cells with infrared absorption spectra acquired from individual cells in at least one reference cell sample to provide comparison data for the single cells;

(c) generating scores for the absorption data using the comparison data;

(d) establishing a mean of the scores for the single cells;

(e) comparing the mean with a normal distribution curve of scores, to detect the chemical differences in the cell sample.

In a third aspect, the invention is a method for detecting chemical differences between a cell sample and a reference cell sample utilizing infrared spectroscopic imaging, the method comprising:

(a) directing a beam of infrared light at a cell sample to produce absorption data, substantially simultaneously, for each of a plurality of single cells in the cell sample;

(b) comparing the absorption data for each of the single cells with a reference set of absorption spectra acquired from individual cells in at least one reference cell sample to provide comparison data for each of the single cells in the cell sample.

In a fourth aspect, the invention is a method for identifying women at high risk for developing cervical dysplasia utilizing single-cell infrared microspectroscopy, the method comprising:

(a) directing a beam of infrared light at single cells in a cervical cell sample to produce absorption data for each of the single cells;

(b) comparing the absorption data from the diagnostic cervical cell sample with a reference set of absorption spectra to identify the woman at high risk for developing cervical dysplasia, the reference set comprising;

absorption spectra from individual cervical cells in cervical cell reference samples taken from women having no history of dysplasia, each of the reference samples having a combination of individual cells exhibiting at least one first spectrum pattern and at least one second spectrum pattern differing from each other in either source or pattern.

DETAILED DESCRIPTION OF THE INVENTION

Abbreviations and Definitions

Figure 1:
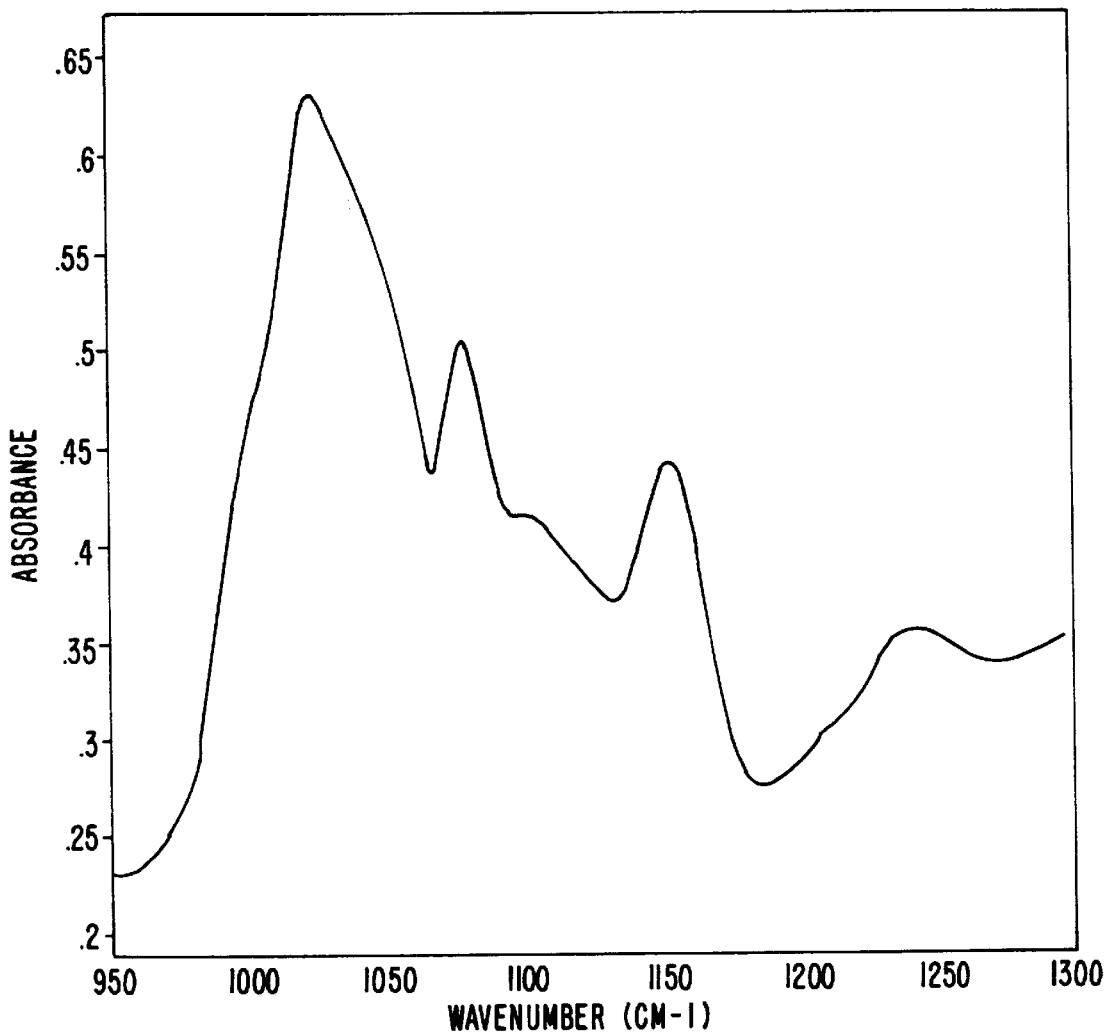
FIG. 1 shows the mid-infrared spectrum (from 950 cm$^{-1}$–1300 cm$^{-1}$) of a normal cervical scraping.

Abbreviations used herein have the following meanings: PCA, principal component analysis; PCR, principal component regression; PLS, partial least squares analysis; PRESS, prediction residual error sum of squares; FT-IR, Fourier Transform infrared spectroscopy; SPIFF, spectral image files; FPA, focal plane array; CIN, cervical intraepithelial neoplasia; HPV, human papilloma virus, MCT, mercury-cadmium-telluride; InSb, indium antimonide; DTGS, deuterated triglycine sulfate.

As used herein, the term "cell sample" denotes the collection of cells which is studied using the methods of the invention. A "cell sample" is, for example, a smear, biopsy sample or pathology sample. The "cell sample" is placed on an infrared-transparent matrix and used as isolated or is further manipulated (e.g., dispersed, preserved, etc.) as desired. Throughout the specification, the word "cell" refers to individual cells which when grouped together with other cells comprise a "cell sample." The phrase "cells of interest," as used herein, defines those cells which have been collected from a population of cells and which are studied by comparing them, using the methods of the invention, to a reference cell sample. Cell samples which are "normal" are those taken from a patient with no prior history of disease. "Normal-dysplastic cells" are those which appear normal by Pap cytology, but which are taken from patients with a history of dysplasia. The term "chemical differences" refers to alterations in cellular chemistry which are associated with, for example, a disease state (e.g., cancer, dysplasia, etc.). These "chemical differences" give rise to a cellular milieu which is altered from that of normal cells and this alteration is detectable by infrared spectroscopy.

The expression "infrared light" is intended to encompass energy in the infrared region of the electromagnetic spectrum. Throughout this specification the terms "spectra" and "absorption data" are used interchangeably. It is understood that either of these terms can refer to the raw data generated by the spectroscopic measurement, a fully processed spectrum or a spectrum which has undergone additional manipulation such smoothing or derivatization. As used herein, the terms "underivatized" and "unsmoothed" are used to refer to a process whereby no arithmetic manipulations have been applied to 1) enhance the slope or changes in the slope of spectra, and 2) reduce the random noise in spectra, respectively.

Spectra acquired practicing the instant invention are processed, manipulated or analyzed by a number of methods including both classical spectroscopic analytical methods and multivariate analysis. As used herein, the term "classical spectroscopic analytical methods" denotes methods such as, for example, analysis and/or comparison of peak heights, peak areas, peak intensities and analysis and/or comparison of ratios of any of these parameters (e.g., peak height A:peak height B, peak height A:peak intensity B, peak height A:peak area A, etc.). Also include in the term "classical spectroscopic analytical methods" is the use of the K-matrix, the P-matrix and/or linear discriminant analysis. The term "multivariate analysis" as used throughout, denotes a method of data analysis such as, for example, PCA, PLS 1, PLS 2 and PCR. The word "mean," as used herein, denotes the arithmetic mean (i.e., the mean obtained by adding several quantities together and dividing the sum by the number of quantities). As used herein, the word "score" denotes quantities derived from processing spectral data by either classical spectroscopic analytical methods or multivariate analysis. A "score" is any quantity which is used to compare a spectrum, or spectra, from a diagnostic cell sample with a reference set of spectra (e.g., peak height, peak height:peak area, etc.). "Predicted scores" are a product of multivariate analysis and are generated by assigning different dummy variables to the spectra of cells falling into known categories of reference spectra (e.g., spectra associated with cells identified as normal, normal-dysplastic, dysplastic, malignant, etc.). The predicted scores indicate how closely the infrared spectra resemble the various known categories of reference spectra. "Frequency distribution profiles" are tabulations of the frequencies of the predicted scores for each biological specimen.

Description of the Embodiments

In the description which follows, human cervical cells are used as an example of a cell type with which the methods of the instant invention can be practiced. The exemplary use of human cervical cells is intended neither to limit nor restrict the scope of cell types with which the present invention can be used. Further, the instant invention can be used with cell samples derived from animals other than human. It will be clear to those of skill in the art that the methods of the instant invention will be of use with a wide range of cell types from an array of different tissues. Detection of altered cellular chemistry in cell samples (e.g., biopsy, surgical pathology samples, etc.) and cultured cells is encompassed by the instant invention.

I. Cells and Tissues

A. General Considerations

The present invention is directed to detecting chemical differences between cells in a cell sample and cells in a reference cell sample. The chemical differences between the cell sample and the reference cell sample can arise from any process known to cause chemical changes in cells. Different cell types can possess inherent chemical differences which are spectroscopically accessible. In certain embodiments of the invention, the chemical differences arise as a result of a disease state in the tissue under study (e.g., cancer, dysplasia, hypertrophy, etc.). The disease state is one caused by a pathogen (e.g., bacteria, virus, fungus, etc.), an insult or a toxin, or can arise due to a genetic anomaly (e.g., multiple sclerosis, cystic fibrosis, etc.). Chemical differences in cells may also arise due to the action of agent or an environmental condition upon the cell.

The methods of the invention can also be used to monitor the course of a disease state which is progressing, resolving or in steady-state. For example, as the disease state progresses, the spectral data acquired from the cells of interest will diverge more sharply, over time, from the spectral data acquired from normal cells which serve as a reference. In contrast, as a disease state resolves, the spectral data from the cells of interest will converge on the spectral data acquired from the normal reference cells. Also within the scope of the invention is the study of tissue in which the disease state is in remission. The invention can also be practiced using diseased cells as the reference cells.

In other embodiments, the chemical differences, or the changes in the chemical differences over time, are due to the treatment of a disease state. The treatment can take any form known to those of skill in the art. For example, the effects of treating cancer with drug therapy, radiation, hyperthermia, hypothermia, cryosurgery, etc. can be monitored using the techniques of the instant invention. Further, following surgical excision and/or treatment of a cancerous lesion, samples taken from the remaining lesion and/or the tissue which surrounded the lesion can be examined for the presence or absence of chemically aberrant cells. The methods of the invention are not limited; however, to use in conjunction with cancer. It will be apparent to those of skill in the art that the methods provided herein are not limited to distinguishing between malignant and normal tissues and cells are useful with tissue in any disease state which gives rise to a spectroscopically detectable chemical difference between the diseased and the normal cells.

The scope of the instant invention includes probing chemical changes in cells which arise as a result of, for example, administration of pharmaceutical agents (e.g., chemotherapeutic agents, agents which alter cellular metabolism, antibiotics, antiviral agents, antifungal agents, anti-inflammatory agents, etc.), administration of carcinogenic or mutagenic agents. Other agents which, when administered to cells, will cause detectable chemical changes will be apparent to those of skill in the art. In certain embodiments, the chemical change is due to the presence of a drug or a probe which is itself detectable as a chemical species by the methods of the present invention.

In further embodiments, the reference set of absorption spectra will be collected from the spectra of a normal, or undamaged tissue, and the diagnostic absorption data will be acquired from a diseased or damaged tissue. Monitoring the effect of a treatment regimen by comparing the treated tissue with the normal tissue is also within the scope of this embodiment. Alternatively, the reference set is assembled from spectra of the diseased or damaged tissue and the course of treatment followed by comparison of the treated tissue with this reference set.

Also within the scope of the present invention is the detection of altered cellular chemistry induced by environmental conditions such as, for example, hyperthermia, hypothermia and ionizing radiation.

The cell or tissue sample comprising the reference set and/or the cell of interest can originate from the tissue of any living organism including, for example, mammals (e.g., humans, domestic animals, farm animals), fish, plants, fungi, etc. In embodiments wherein the cells or tissue are derived from mammals the tissue is from any structure or organ system within the body including, but not limited to, bladder, breast, male or female reproductive system (e.g., prostate, testicles, ovaries, uterus, cervix, etc.), central nervous system, blood, liver, bone, colon, pancreas or skin.

B. Sample Preparation

The discussion which follows is equally applicable to the preparation of the cell sample comprising the cells of interest as it is to the preparation of the reference cell sample(s). The cell or tissue sample is collected and prepared by any of the methods known in the art. For example, tissue and cell samples are taken from biopsy samples, scrapings or from pathology samples following surgical excision. Samples are prepared as standard histology or cytology samples and can be fixed and/or preserved and/or stained. Cell samples can be dispersed on a substrate. Preferably, non-diagnostic debris is removed from cell or tissue samples. Alternatively, the cell or tissue samples are utilized as isolated, and without further preparation, to acquire IR spectroscopic data. By way of illustration, when the methods of the invention are practiced using cervical cells, the exfoliated cervical cell sample are collected by standard methods such as those used in collecting samples for Pap screening or biopsy and applied to an infrared transparent-matrix.

A variety of infrared-transparent matrices are available for use in the present invention. Preferred matrices for mid-infrared studies are $BaF_2$, ZnS, polyethylene film, CsI, KCl, KBr, $CaF_2$, NaCl and ZnSe. In certain embodiments, once the sample is applied to the matrix, the sample is dried to remove moisture which interferes with the infrared spectra. The methods used for drying will typically involve air-drying at ambient temperatures. Alternatively, the sample is dried with controlled gentle heating, and by passing a stream of air or inert gas over the sample. For example, matrices with applied samples are placed at 30° C. to 35° C. (e.g., a hot plate with temperature control knob to about 30–35° C.)

and an atmosphere of, for example, air, nitrogen or argon can be passed over the samples to expedite their drying.

Others have utilized a sample holder described in U.S. Pat. No. 4,980,551. Briefly, that device is made to accommodate a set of IR transparent windows in face to face contact, and contains the means to secure the windows in the path of an infrared light beam. The exterior of at least one of the windows has a surface portion contoured to provide a space between the windows for the sample. To utilize the holder, contents from a cervical scraping are first deposited in the sample space of one of the windows. With the other window carefully positioned over the specimen, the holder is tightened to secure the windows. Infrared light is passed through the sample space and the absorption of the cervical sample is recorded. Acquisition of spectra of cervical specimens by this technique is a difficult and time consuming process. For example, it is not only required that special windows be made, but also the biological specimen must remain undisturbed while being compressed between two windows. Compression frequently causes the leakage of tissue fluids, and ultimately the spilling of cervical specimens beyond the confines of the windows. Moreover, because cervical specimens can be contaminated with infectious agents such as the AIDS, Herpes and/or the various Hepatitis viruses, any leakage creates serious biological safety concerns. Still further, tissue fluids also absorb strongly in the mid-infrared region and contribute to changes in intensity at several frequencies.

In contrast, the methods of the present invention use samples that are easy to manipulate and which provide high quality spectra. More importantly, drying eliminates the problems associated with tissue fluids, and reduces the risk of contamination by infectious agents. In a study of more than 100 cervical scrapings processed by this method, the direct deposition and drying of specimens was found to provide spectra with minimal or no fringes.

Clumping of cells in a cervical smear or other tissue sample is generally problematic and complicates the diagnosis. A thorough dispersion of the cell sample causes the separation of cells from surrounding nondiagnostic debris and mucus, provides a relatively uniform suspension of cells for spectral acquisition, and enhances the possibility of detecting the abnormal cells. Thus, in some embodiments, the samples will be dispersed prior to their application to the infrared matrix. Dispersion of the cell sample is preferably carried out in a preservative solution which maintains the integrity of the exfoliated cells. The selection criteria for a preservative solution also necessitate that the preservative solution evaporates readily, and upon evaporation, leaves no residues that create interference in the infrared spectra of cervical scrapings. An example of one such preservative solution is PRESERV CYT® (CYTYC Corporation, Marlborough, Mass., USA). Other solutions will be apparent to those of skill in the art and can include standard solutions such as, for example, ethanol/water mixtures, formalin, Carnoy's fixative, etc. The methods of the present invention can also be practiced on tissue and cell samples which are not preserved. Following dispersion of the cell sample, the mixture is filtered to remove the nondiagnostic debris and the solution of cells is applied in a uniform layer to an infrared matrix, as described above, and dried.

II. Instrumentation and Exemplary Protocol

A. Single-Cell Microspectroscopy

Once the sample for diagnosis has been prepared on the infrared matrix, a beam of infrared light, preferably mid-infrared light, is directed at individual cells within the sample and the absorption of the sample is monitored using any of a number of commercially available infrared spectrometers. An example of an appropriate instrumental setup is a Bio-Rad Digilab FTS 165 spectrometer coupled to a Bio-Rad FT-IR UMA-500 microscope. Other suitable spectrometers and microscopes are known to those of skill in the art. Detectors useful in practicing the instant invention include, for example, a single-element MCT (mercury-cadmium-telluride) detector or an array detector.

A fundamental advantage of FT-IR microspectroscopy lies in the spatial selectivity of the procedures. The spatial selectivity can be better understood by way of comparison with bulk IR spectroscopy. In bulk spectroscopy, the IR beam is directed towards all components of a cell sample, cellular and non-cellular, and no specific components or cells in the cell sample can be targeted for spectral acquisition. Consequently, in bulk spectroscopy, the final spectrum represents the average spectra of all components in a cell sample. In microspectroscopy, on the other hand, the IR beam is directed towards any of several objects within a smear. For example, if the spectra of only red blood cells are desired, the microscope stage is simply moved so as to position the red blood cells in the path of the IR beam. In addition to its ability to select objects, FT-IR microspectroscopy is also a sensitive method allowing the study of objects with sizes approaching the diffraction limit. Thus, in a cell sample comprising cervical cells, for example, this method can provide a spectrum of each type of cervical cell; whether be it a 7–12 micron parabasal, or endocervical cell, or a 35–45 micron intermediate squamous epithelial cell.

IR microspectroscopy, demonstrates that the infrared spectra of individual cells allow the chemical changes in a cell sample to be detected. For example, it is the infrared spectra of individual cervical cells in a cervical cell scraping that are useful for the discriminating between normal, dysplastic and malignant cervical scrapings. More importantly, techniques have been developed and are described herein (see Examples 1–5), for constructing distribution profiles of spectra of individual cells based on predicted scores generated by Principle Component Analysis (PCA) and Partial Least Squares (PLS). The distribution profiles are used to diagnose normal cells and chemically aberrant cells in a cell sample. Chemically aberrant cells can include cytologically normal and cytologically abnormal cells. The distribution profiles allow the cells to be classed according the presence or absence of distinctive chemical changes associated with disease states. For example, distribution profiles generated from cervical cell samples display a separation between the spectra of cytologically "normal" cells in "normal" smears (i.e., smears that were cytologically diagnosed as normal and which were derived from women with no prior history of dysplasia) and in smears with "normal-dysplasia" (i.e., smears that were cytologically diagnosed as normal and which were derived from women with a past history of dysplasia). Similarly, the methods of the present invention allow separation between the spectra of "normal" cells in "normal" smears and cytologically "normal" cells in smears diagnosed as cancer.

The infrared spectra are generally collected at a resolution of from about 2 cm$^{-1}$ to about 10 cm$^{-1}$, preferably from about 4 cm$^{-1}$ to about 8 cm$^{-1}$. Additionally, a number of scans are taken and co-added. Preferably about 50–1000 scans are co-added, more preferably about 100–800 scans are co-added. In general, the spectra are normalized by setting the minimum absorbance at 0.0 and the maximum absorbance at 1.0 in the frequency regions between 3000 cm$^{-1}$ to 950 cm$^{-1}$; however, in some embodiments, the techniques of the invention are practiced without normalizing the spectra. In one group of embodiments, the data is neither smoothed nor derivatized. In yet another group of embodiments, the data is smoothed but not derivatized or derivatized but not smoothed. In other embodiments the data is smoothed and/or derivatized. Thus, in one group of embodiments the data is first smoothed then derivatized. In another group of embodiments, the data is first derivatized then smoothed.

In the embodiment of this method utilizing cervical cell samples, the reference set of infrared absorption data is obtained from cell samples which have previously been identified by Pap cytology as normal, dysplastic or malignant samples. Preferably, the reference set of infrared absorption data from cervical cells is obtained from a representative group of females with varying degrees of cervical conditions including, but not limited to dysplasia and cancer. Identification of these cell types is typically made by cytological examination such as the one performed on cervical smears. More preferably, the reference set of infrared absorption data is prepared from about 10 to about 1000 reference cell samples. The infrared absorption spectra for each of the identified cell types is preferably obtained for the mid-infrared region from about 3000 cm$^{-1}$ to about 950 cm$^{-1}$. In the near IR, use of the frequencies between 12,500 cm$^{-1}$ to 4000 cm$^{-1}$ is preferred. In those embodiments of the invention utilizing light in the near infrared region, sample holders are used which are made of a material appropriate for use in this region such as those made of glass, quartz or CaF$_2$.

The number of individual cells, present in each reference cell sample, on which spectroscopy is performed, is preferably from about 10 to about 1000 and more preferably from about 100 to about 500. It will be appreciated by those of skill in the art that both the number of cell samples and the number of cells within those cell samples which are spectroscopically studied can be varied over a wide range. As it becomes larger (i.e., more cell samples and more cells) the reference set becomes a more accurate portrayal of the spectrum of a particular cell type. Thus, it is desirable to vary the size of the reference set to achieve as adequate a portrayal of the cell type as is necessary under the circumstances.

In certain embodiments, the chemical difference is associated with a malignant or premalignant phenotype. In further preferred embodiments, the cell sample comprises cervical cells which are premalignant and/or malignant. In embodiments, utilizing cervical cells, comparison of the infrared absorption data for the sample and the data for the reference set preferably utilizes principal component analysis in the frequency region of about 3000 cm$^{-1}$ to about 950 cm$^{-1}$ and more preferably in the frequency regions of about 1250 cm$^{-1}$ to 1000 cm$^{-1}$, about 1420 cm$^{-1}$ to 1330 cm$^{-1}$ and about 3000 cm$^{-1}$ to 2800 cm$^{-1}$.

B. Infrared Spectroscopic Imaging

Recent technological advances in infrared spectrometer detector technology have made possible the development of infrared spectroscopic imaging. The application of infrared spectroscopic imaging to the analysis of cells in a cervical cell sample is discussed herein.

Vibrational spectroscopic imaging is a comparatively new imaging modality with utility in the biological, chemical and material sciences (Lewis, E. N., et al. *Anal. Chem.*, 67:3377–3381(1995)). A flexible and robust technique, vibrational spectroscopic imaging combines the molecular identification powers of spectroscopic molecular analysis with the ability to visualize the morphology and regional chemical properties of a tissue sample through 2-D and, potentially, 3-D imaging. Further, vibrational spectroscopic imaging provides access to both qualitative and quantitative data about the distribution of the molecules of interest in the sample under investigation.

A typical near-IR imaging instrument utilizes a step-scan Fourier transform Michelson interferometer (Bio-Rad FTS-60A) coupled to an IR microscope (Bio-Rad UMA 500A) and an indium antimonide (InSb) focal plane array (FPA) detector (ImagIR, Santa Barbara Focalplane). The microscope optics and the interferometer electronics are modified to couple efficiently to the InSb detector. The optical modification consists of placing a CaF$_2$ lens between the microscope objective and the FPA. The electronic modification consists of adding a counter/timer board which synchronizes the stepping of the interferometer and the FPA detector. Data acquisition and processing is similar to that performed during a conventional FT-IR study. Briefly, the interferograms are organized as spectral image files (SPIFF) and Fourier transformed. The SPIFF files can be visualized using commercially available image processing and visualization software (e.g., ChemImage 1.0, ChemIcon, Optimas 4.02, etc.). A typical mid-IR imaging system will have many of the same components described above, but will differ in that the FPA can be a MCT (mercury cadmium telluride) detector. Also, the lens between the microscope objective and the detector can be CaF$_2$, glass or quartz.

Infrared spectroscopic imaging instruments are commercially available, e.g., Bio-Rad's FTS StingRay 6000 (Bio-Rad, Cambridge, Mass.). Infrared imaging is made possible by combining the multiplexing power of interferometry with a multichannel detector. The multichannel detector allows spectra at every pixel to be collected simultaneously and the interferometer allows all relevant wavelengths to be monitored concurrently. Currently, state-of-the-art FPA detectors have as many as one million detector elements and readout rates in excess of 16,000,000 pixels per second. The resolution of the images produced in IR imaging is limited only by the number of detector elements on the FPA. In addition, the FPA detectors can be constructed of materials that are sensitive to light in the wavelength range between 10,000 cm$^{-1}$–500 cm$^{-1}$. Finally, although a great quantity of data is collected in the typical IR imaging experiment (a 128×128 detector array gives 16,384 pixels) the multiplex/multichannel instrument set up affords rapid data acquisition. For example, Lewis and coworkers have reported collecting data sets containing 16,384 pixels at 16 cm$^{-1}$ resolution in only 12 seconds (Lewis, E. N., et al. *Anal. Chem.*, 67:3377–3381 (1995)). The use of infrared spectroscopic imaging instruments such as the FTS StingRay 6000, above, equipped with optic fibers finds application with dried cell samples, in vivo imaging, and cell samples in a preservative fluid.

In the infrared spectral imaging approach, an infrared-sensitive "camera," comprised of a two-dimensional array of detectors, captures an image of the field of view of the infrared microscope. Each detector in the array captures one pixel of the image. The data from each pixel consists of the entire infrared absorption spectrum for that point in the image, over the spectral range specified. The result of this process is a large data file which contains the complete spectrum of each pixel in the image. The field of view of the microscope and the camera are adjusted so that the image of a typical cell of interest covers at least 9 pixels. Collection of this data takes a very short time, typically seconds to minutes. Since the data is being collected over the entire image, all the data necessary for a diagnostic test is acquired simultaneously; a process denoted by the term "multiplex advantage."

To obtain usable diagnostic results from the infrared spectroscopic imaging process, it is preferable to obtain spectra from approximately 100 cytologically normal cells, and then to extract from this set the spectra of those cells which meet the criterion being used for the evaluation (e.g., either Pattern I or Pattern II). In contrast, in the single cell microspectroscopic method, the cells are identified by the operator through the microscope, the spectra are obtained one at a time, and the spectra are then examined by the operator and classified as to pattern. The spectra of those cells which exhibit the appropriate pattern are then analyzed by the chemometric software. In the imaging approach, the spectra of the entire image are obtained simultaneously by the instrument and stored in a computer. These spectra are then examined by software to: first, locate individual cells and group the several spectra obtained from each cell; second, classify the located cells as to pattern; and third, compare the spectra of the appropriate pattern against the reference set. This process can be carried out entirely automatically in software, and can be completed in a very short time. The output of the imaging process is a completed diagnosis, since it yields the scores for each of the cells which were spectroscopically probed.

The imaging aspect of the invention can be performed using either mid- or near-infrared light. When the imaging is performed using mid-infrared light, the beam of infrared light has a frequency of from about 3000 cm$^{-1}$ to about 950 cm$^{-1}$. When performed using near infrared light, the beam of infrared light has a frequency of from about 4000 cm$^{-1}$ to about 12000 cm$^{-1}$.

III. Data Processing

After collection of the infrared absorption data for the single cells in the cell sample, the data is compared to the reference set of spectra, acquired under the same experimental spectroscopic conditions, to determine if variations exist in the spectra which are characteristic of chemical differences. In preferred embodiments, the chemical changes are due to a malignant or premalignant condition. A number of means of performing this comparison are used. In preferred aspects of the present invention, multivariate analysis is used.

Discrimination between spectra of specimens that have subtle variations requires the use of robust and sensitive methods of analysis. These methods must model for the nonlinearities that can arise due to various causes as well as account for the day to day drifts in instrument settings. Sample handling errors, spectral fringes, baseline shifts, batch to batch variations, the presence of nondiagnostic debris and all other factors that adversely affect discrimination must be also adequately accounted for and modeled. Water absorbs strongly in the mid-infrared region and contributes to changes in intensity at several frequencies. Thus, the method of analysis must also consider the varying amounts of moisture in cervical specimens. Lastly, for a method to prove robust it must distinguish between good and poor quality spectra, and exclude samples not representative of the reference set. The non-representative samples are referred to as outlier samples. An outlier sample is a sample that is statistically different from all other samples in the reference set. In the case of cervical scrapings, an outlier spectrum can result from samples with less than an optimal number of cells, and/or specimens that are rich in blood, mucus and/or nondiagnostic debris.

In general, the reference set should be representative of all expected variations in the spectra. The infrared absorption data of all samples is then processed using methods such as, for example, classical methods of spectroscopic analysis or multivariate analysis.

Classical techniques of spectroscopic analysis rely on such spectral characteristics as peak height, peak shape, peak area, peak intensity and ratios of these characteristics. The ratios may be taken between peak characteristics derived from the same peak or from peak characteristics derived from different peaks. Once a first ratio is taken, a second ratio may be taken between the first ratio and another spectral characteristic or the first ratio and another ratio of spectral characteristics. Other methods of data analysis of use in practicing the instant invention include, for example, the K-matrix, the P-matrix and linear discriminant analysis. Data analysis methods in addition to those enumerated above will be apparent to those of skill in the art.

Multivariate analysis has been used to analyze biological samples. For example, Robinson, et al. in U.S. Pat. No. 4,975,581 (issued Dec. 4, 1990) describe a quantitative method to determine the similarities of a biological analyte in known biological fluids using multivariate analysis. In contrast to the instant invention, Robinson, et al. describes the in vivo evaluation of analytes in fluids, and uses non-invasive techniques. No accommodations are made to discriminate between solid biological material such as mammalian cells or to address the issues that can arise while discriminating the IR spectra of solid biological materials with varied path lengths outside the body. Nevertheless, multivariate analysis is a useful method of data analysis in the methods described and claimed herein.

Principal Component Analysis (PCA) and discriminate analysis has recently been employed to distinguish between normal and abnormal cervical scrapings. See, Ge, et al., *Applied Spectroscopy* 49:432–436 (1995). However, the methods described therein did not describe single-cell microscopy nor did it rely on the removal of interfering and nondiagnostic material from the cervical specimens. Further, Ge, et al. also relied on preprocessing algorithms that smoothed the spectra. Smoothing of spectra can obscure the subtle differences which exist between spectral patterns, and consequently can affect the discriminate analysis.

Haaland, et al., in U.S. Pat. No. 5,596,992 (issued Jan. 28, 1997) teach the use of multivariate methods to detect differences between normal and malignant cell samples. Haaland, et al. do not describe any single-cell infrared microscopy. Further, Haaland, et al. teach that the spectra have to be preprocessed by linear base-line corrections and subtracting water vapor absorptions.

Although PCR and PLS have been used in various fields of science and in many types of applications, these techniques have never been used to discriminate in the mid-infrared region of the spectra, chemical differences between single cells in diagnostic samples and single cells in reference samples. Both PCR and PLS can reduce massive amounts of data into sets that can be readily managed for analysis. More importantly, when these methods are used to evaluate the spectra of mammalian cells, the techniques analyze entire regions of a spectrum and allow discrimination between the spectra of different groups of specimens.

In the present invention, when multivariate analysis is used, the comparison of absorption data is typically carried out by a partial least squares (PLS) or principal component analysis (PCA) statistical method on data which can be preprocessed (i.e., smoothed and/or derivatized), but which is preferentially unsmoothed and underivatized. Preferably, comparisons using principle component regression (PCR) are carried out using PCA. A number of computer programs are available which carry out these statistical methods, including PCR-32® (from Bio-Rad, Cambridge, Mass., USA) and PLS-PLUS® and DISCRIMINATE® (from Galactic Industries, Salem, N.H., USA). Discussions of the underlying theory and calculations can be found in, for example, Haaland, et al., *Anal. Chem.* 60:1193–1202 (1988); Cahn, et al., *Applied Spectroscopy*, 42:865–872 (1988); and Martens, et al., MULTIVARIATE CALIBRATION, John Wiley and Sons, New York, N.Y. (1989). Both PCR and PLS use a library of spectra derived from single cells of a reference cell sample to create a reference set, wherein each of the spectra are acquired under identical conditions. The data analysis techniques consist of spectral data compression (in the case of PCR, this step is known as PCA), and linear regression. Using a linear combination of factors or principal components, a reconstructed spectrum is derived. This reconstructed spectrum is compared with the spectra of unknown specimens which serves as the basis for classification.

In certain aspects of the present invention the predicted scores generated for individual cells are "averaged" over the sample. When more than one sample is used, the "averaged" score from the individual cells over the sample are "averaged" over the collection of samples. The method of "averaging" can consist of simply taking the arithmetic mean of the predicted scores or can rely on other statistical methods for determining population distributions known in the art. The methods include, for example, determining the median and determining the mean of the predicted score population. The extent to which a population is scattered on either side of the determined center is assessed by establishing a measure of dispersion such as, for example, the standard deviation, the interquartile range, the range and the mean deviation. Other methods, of use in practicing the present invention, for establishing both the "average" value for the population of prediction scores and the extent of population scatter will be apparent to those of skill in the art.

Prior to the analysis of unknown samples, another set of spectra of the same materials are typically used to validate and optimize the reference. This second set of spectra enhance the prediction accuracy of the PCR or PLS model by determining the rank of the model. The optimal rank is determined from a range of ranks by comparing the PCR or PLS predictions with known diagnoses. Increasing or decreasing the rank from what was determined optimal can adversely affect the PLS or PCR predictions. For example, as the rank is gradually decreased from optimal to suboptimal, PCR or PLS would account for less and less variations in the reference spectra. In contrast, a gradual increase in the rank beyond what was determined optimal would cause the PCR or PLS methodologies to model random variation rather than significant information in the reference spectra.

Generally, the more spectra a reference set includes, the better is the model, and the better are the chances to account for batch to batch variations, baseline shifts and the nonlinearities that can arise due to instrument drifts and changes in the refractive index. Errors due to poor sample handling and preparation, sample impurities, and operator mistakes can also be accounted for so long as the reference data render a true representation of the unknown samples.

Another major advantage to using PCR and PLS analysis is that these methods measure the spectral noise level of unknown samples relative to the reference spectra. Biological samples are subject to numerous sources of perturbations. Some of these perturbations drastically affect the quality of spectra, and adversely influence the results of a "diagnosis". Consequently, it is preferable to distinguish between spectra that conform with the reference spectra, and those that do not (e.g. the outlier samples). The F-ratio is a powerful tool in detecting conformity or a lack of fit of a spectrum (sample) to the reference spectra. In general F-ratios considerably greater than those of the reference indicate "lack of fit" and should be excluded from the analysis. The ability to exclude outlier samples adds to the robustness and reliability of PCR and PLS as it avoids the creation of a "diagnosis" from inferior and corrupted spectra. F-ratios can be calculated by the methods described in Haaland, et al., *Anal. Chem.* 60:1193–1202 (1988), and Cahn, et al., *Applied Spectroscopy* 42:865–872 (1988).

When discriminating between samples of different cell specimens (e.g., cervical scrapings), the biological materials no longer have known concentrations of constituents, and/or a constant path length. As a result, the reference spectra should determine the range of variation allowed for a sample to be classified as a member of that reference, and should also include preprocessing algorithms to account for diversities in path length. One normalization approach that aids in the discrimination of cervical specimens is locating the maximum and minimum points in a spectral region, and resealing the spectrum so that the minimum remains at 0.0, and the maximum at 1.0 absorbance (e.g. in the frequency region between 3000 cm$^{-1}$ to 950 cm$^{-1}$). Another normalization procedure is to select a specific peak(s) at a certain frequency(ies) of the IR spectra, and relate all other peaks to the selected peak(s). A third type of normalization is to normalize the magnitude of the absorbance vector before processing.

Known infrared spectroscopic techniques have relied on bulk analysis of samples. Conclusive identification of those individual cells that contribute to the changes in the spectra between normal and abnormal specimens remains an important objective; however, bulk spectroscopy does not afford access to this information. The techniques and methods of certain aspects and embodiments of the present invention combine the spatial resolution of single-cell microscopy with infrared spectroscopy's powerful ability to probe the chemical structure and/or environment of a sample. The methods of one aspect of the present invention are carried out using a beam of mid-infrared light which is directed through an aperture of individual cell size, thereby providing absorption data for single cells.

Thus, in a first aspect, the invention provides a method for detecting chemical differences between a cell sample and a reference cell sample, utilizing single-cell infrared microspectroscopy, the method comprising:

(a) directing a beam of infrared light at single cells in a cell sample to produce absorption data for each of the single cells;

(b) comparing the absorption data for each of the single cells with infrared absorption spectra acquired from individual cells in at least one reference cell sample to provide comparison data for each of the single cells in the cell sample.

In this aspect of the invention, the beam of infrared light is preferably directed from a source located within the spectrometer through the sample adsorbed onto an infrared-transparent matrix. The infrared light impinges on a detector, whereby the absorption data is produced. The absorption spectra for the reference sample is produced using a substantially similar method.

In preferred embodiments, the reference sample and the cells of interest are from human tissue. In still more preferred embodiments, the tissue is isolated from the cervix. In those embodiments of the invention utilizing cervical cells, the beam of infrared light has a frequency of from about 3000 cm$^{-1}$ to about 950 cm$^{-1}$. An important feature of this aspect of the invention is that the cervical cells of the reference set are cytologically determined to correspond to a normal, malignant or premalignant phenotype. In a preferred embodiment, the cell sample is a cervical cell sample and the phenotype of the cells in the reference set is determined by standard methods (e.g., Pap cytology, biopsy, etc.).

In certain preferred embodiments, the comparison data is used to generate scores for the absorption data and the scores are then used to construct frequency distribution profiles. In still other preferred embodiments, the scores are generated using multivariate analysis and the scores are predicted scores. In still other embodiments, the methods of classical spectroscopic analysis are utilized to generate the scores.

The infrared spectra are generally collected at a resolution of from about 2 cm$^{-1}$ to about 10 cm$^{-1}$, preferably from about 4 cm$^{-1}$ to about 8 cm$^{-1}$. Additionally, a number of scans are taken and co-added. Preferably about 50–1000 scans are co-added, more preferably about 100–800 scans are co-added. In general, the spectra are normalized by setting the minimum absorbance at 0.0 and the maximum absorbance at 1.0 in the frequency regions between 3000 cm$^{-1}$ to 950 cm$^{-1}$; however, the techniques of the invention can be practiced without normalizing the spectra. In other embodiments the data is smoothed and/or derivatized; however, the invention can be practiced using spectral data which is unsmoothed and/or underivatized. In those embodiments of the invention wherein the data is smoothed and/or derivatized, the steps of smoothing and derivatizing can be carried out in any order.

The comparison of the absorption data and the reference absorption spectra is made using any technique or instrumentation known to those of skill in the art for comparing spectral data sets. In certain preferred embodiments, utilizing cervical cells, comparison of the infrared absorption data for the sample and the data for the reference set utilizes principal component analysis in the frequency region of from about 3000 cm$^{-1}$ to about 950 cm$^{-1}$. In certain more preferred embodiments the comparison is conducted in the range of from about 1200 cm$^{-1}$ to about 1000 cm$^{-1}$, more preferably in the frequency regions of from about 1250 cm$^{-1}$ to about 1000 cm$^{-1}$, from about 1420 cm$^{-1}$ to about 1330 cm$^{-1}$ and from about 3000 cm$^{-1}$ to about 2000 cm$^{-1}$. In still other preferred embodiments, the spectral data is unsmoothed and underivatized. In other preferred embodiments, the data analysis technique utilizes multivariate analysis.

In preferred embodiments of this aspect, the number of cells from which spectra are acquired is from about 10 to about $10^6$ and is more preferably from about 10 to about 1000. The number of cell samples whose predicted scores constitute the calculated mean is preferably from about 2 to about 1000. In still other preferred embodiments, the reference sample and the sample are substantially freed of non-diagnostic debris and dried on the infrared matrix prior to initiating the spectroscopic studies.

In other preferred embodiments of this aspect, the chemical differences arise as a result of a disease state in the cells or tissue being studied. The disease state is a malignancy or any of an array of diseases caused by a pathogen (e.g., bacteria, virus, fungus, etc.), an insult or a toxin, or can arise due to a genetic anomaly (e.g., cancer, multiple sclerosis, cystic fibrosis, etc.). In other preferred embodiments, the chemical differences between the cells or tissues of interest and the reference sample are due to the therapeutic treatment of the disease state. In particularly preferred embodiments, the disease state is cancer or dysplasia.

In a second aspect, the invention provides a method for detecting chemical differences between a cell sample and a reference cell sample utilizing single-cell infrared microspectroscopy, the method comprising:

(a) directing a beam of infrared light at single cells in the cell sample to produce absorption data for each of the single cells;

(b) comparing the absorption data for the single cells with infrared absorption spectra acquired from individual cells in at least one reference cell sample to provide comparison data for the single cells;

(c) generating scores for the absorption data using the comparison data;
(d) establishing a mean of the scores for the single cells;
(e) comparing the mean with a normal distribution curve of scores, to detect the chemical differences in the cell sample.

In this aspect of the invention, the embodiments and preferred embodiments are generally the same as those described in connection with the above-detailed embodiment.

In this aspect of the invention the scores generated for individual cells are "averaged" over the sample to produce an averaged score. The scores are generated using the techniques of classical spectroscopic analysis or, preferably, multivariate analysis. In preferred embodiments, using more than one cell sample, the averaged score from each of the cell samples are averaged over the population of cell samples. The method of "averaging" can consist of simply taking the arithmetic mean of the predicted scores or can rely on other statistical methods for determining population distributions known in the art. In preferred embodiments, the averaging is performed by taking the arithmetic mean. When a distribution profile is constructed, the extent to which a population is scattered on either side of the determined center is assessed by establishing a measure of dispersion such as, for example, the standard deviation, the interquartile range, the range and the mean deviation. In preferred embodiments, the standard deviation serves as a measure of the scatter.

In a third aspect, the invention is a method for detecting chemical differences between a cell sample and a reference cell sample utilizing infrared spectroscopic imaging, the method comprising:

(a) directing a beam of infrared light at a cell sample to produce absorption data, substantially simultaneously, for each of a plurality of single cells in the cell sample;
(b) comparing the absorption data for each of the single cells with a reference set of absorption spectra acquired from individual cells in at least one reference cell sample to provide comparison data for each of the single cells in the cell sample.

The techniques of sample preparation and data processing used in the imaging aspect of the invention are generally the same as those described above in connection with infrared microspectroscopy. Further, the different embodiments and uses of this aspect of the invention are generally similar to those detailed above.

One notable difference between the spectroscopic imaging and single-cell microspectroscopic methods is that the former acquires the data from a population of individual cells in a substantially simultaneous manner. "Substantially simultaneously" refers to the ability of this aspect of the invention to acquire spectra for each of a collection of single cells in a cell sample at approximately the same time. This method stands in contrast to methods which use bulk spectroscopy and those aspects of the present invention utilizing single cell microspectroscopy.

In bulk spectroscopy, the spectra of a population of cells is taken simultaneously resulting in an average spectrum for all cells across the sample. Importantly, there is no method to deconvolute the resulting average spectrum to get information for individual cells. In single-cell microspectroscopy, the operator focuses the microscope on a single cell and acquires a spectrum from that cell; the operator then focuses on a second cell and acquires a spectrum for that cell. This process is continued until a spectrum set of the desired size is obtained. Although the microspectroscopic aspect of the present invention affords access to single cell spectroscopic data this technique is time consuming, particularly when multiple acquisitions are required to produce a spectrum. In contrast, the imaging aspect of the present invention provides the capability to simultaneously collect spectra from all of the cells within a selected window of the sample (i.e., a portion of the sample) and to deconvolute the spectral data to arrive at spectra for each of the individual cells within the window.

An additional advantage offered by the imaging aspect of the present invention is the ability to prepare reference sets of absorption spectra which consist entirely of spectra of diseased cells. Typically a cytologist depends on the presence of a few abnormal cells (e.g., malignant, dysplastic, etc.) in a cell sample to arrive at a diagnosis of abnormality. Most often, the diagnosis is arrived at following examination of a cell sample which has been stained. Unstained cell samples, such as those preferred in practicing the instant invention, do not allow the ready differentiation between normal and abnormal cells achieved with stained cell samples. Thus, in the single cell microspectroscopic aspect of the invention, it is generally not possible to locate, with the microscope, the abnormal cells in a sample and construct a reference set of spectra from these cells. In contrast, when using spectroscopic imaging, a window of the sample is imaged and spectra from all of the cells within the window are acquired. Following imaging, the sample is stained and, using the stained sample as a "roadmap" the abnormal cells and their spectra are identified from among the cells in the cell sample and the corresponding collection of spectra, respectively.

The imaging aspect of the invention can also be used for in vivo diagnosis of cellular chemical abnormality. The techniques used in this embodiment are generally the same as described above. Differences are in the fundamental approach of in vivo collection of data and the use of an optic fiber to direct the beam of mid- or near-infrared light. Typical optic fibers used for mid-infrared include chalcogenide and silver halide. A typical optical fiber for near-infrared use is quartz fiber. One advantage to in vivo analysis is that it directs the physician to the site of the anomalous tissue and minimizes the size of the tissue taken for biopsy. Moreover, this method can provide a rapid objective screening of patients in a doctor's office.

In a fourth aspect, the invention is a method for identifying women at high risk for developing cervical dysplasia utilizing single-cell infrared microspectroscopy, the method comprising:

(a) directing a beam of infrared light at single cells in a cervical cell sample to produce absorption data for each of the single cells;
(b) comparing the absorption data from the diagnostic cervical cell sample with a reference set of absorption spectra to identify the woman at high risk for developing cervical dysplasia. In this aspect, the reference set comprises absorption spectra from individual cervical cells in cervical cell reference samples taken from women having no history of dysplasia, each of the reference samples having a combination of individual cells exhibiting at least one first spectrum pattern and at least one second spectrum pattern differing from each other in either source or pattern.

Figure 6:
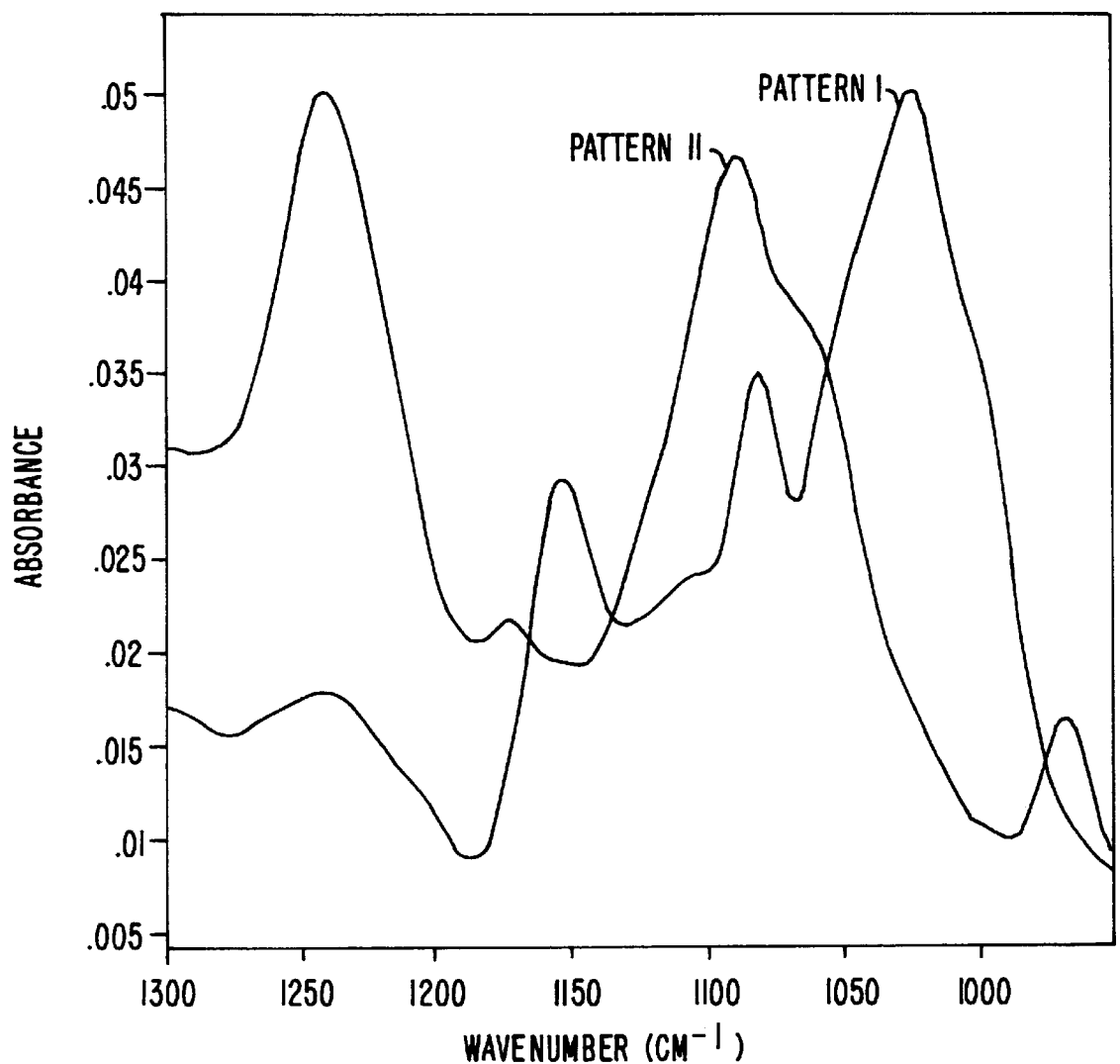
FIG. 6 shows two typical mid-infrared spectra (from 1000 cm$^{-1}$–1300 cm$^{-1}$) of individual normal cells in a cervical smear.

The techniques of sample preparation, data acquisition and data analysis discussed above in conjunction with the other aspects of the present invention are used in conjunction with this aspect of the invention and the preferred embodiments are generally the same as those detailed in conjunction with the other aspects of the invention. Both single cell microspectroscopic and spectroscopic imaging techniques are of use in conjunction with this aspect of the invention. In certain preferred embodiments, the phenotype of the cells in the reference set is determined by standard methods (e.g., cervical biopsy, Pap cytology). In other preferred embodiments, the method uses infrared spectroscopy to generate the first and second spectrum patterns. The reference set of absorption spectra is selected from infrared spectra with patterns corresponding to those defined as Pattern I and Pattern II (FIGS. 6A and 6B, respectively) and linear combinations of Pattern I and Pattern II. In embodiments of this aspect using mid-infrared light, use of the frequencies between 3000 $cm^{-1}$ to 950 $cm^{-1}$ is preferred. In the near IR, use of the frequencies between 12,500 $cm^{-1}$ to 4000 $cm^{-1}$ is preferred.

EXAMPLES

The detailed examples which follow describe the methods of the invention as applied to distinguishing between normal, normal dysplastic, dysplastic and malignant cervical cells which are recovered during a routine cervical smear. The examples describe the use of FT-IR microspectroscopy. The techniques described herein are also applicable to other spectroscopic data collection means including FT-IR spectroscopic imaging.

Although much of the detailed discussion embodied herein relies on the use of cervical cells as a representative example, the use of this cell type is not intended to infer that the methods of the invention have utility with only cervical cell samples. It will be apparent to one of skill in the art that the methods can be extended with slight modification to the analysis of chemical differences between cells and/or diagnosis of disease states, in an array of different cell types. For example, the analysis of chemical changes and/or the diagnosis of disease states in cells of the breast, bladder, male or female reproductive system (e.g., prostate, ovaries, etc.), liver, lymph nodes, bone, pancreas and other organs or structures are within the scope of this invention. The above list is intended to be illustrative and not exhaustive. Thus, the following examples are offered solely for the purposes of illustration, and are intended neither to limit nor to define the invention.

Recent infrared spectroscopic studies of bulk cervical scrapings have revealed marked differences in the spectra of normal and malignant samples. Despite the presence of these differences, their precise origin is unknown. Although it appears intuitively reasonable that changes in the malignant cell per se give rise to the spectral abnormalities associated with cancer, no confirmation of this exists. Still further, it has been observed that in some malignant cervical samples, the cancerous cells constitute no more than 10% of the total number of epithelial cells; yet, their infrared spectra are no different from those with far greater percentages of malignant cells. Without intending to be bound by any particular theory of operation, four possible explanations for such an observation are presented, including: 1) the changes in the cancer cell are so strong that they dominate the spectral contribution of the remaining $90^+\%$ of the cells, 2) the spectral changes originate from another type of cell, 3) cells not identifiable morphologically as malignant by Pap smear have already undergone the same or similar chemical changes as the malignant cell and therefore, together with the bone fide malignant cells constitute the majority of abnormal cells, and/or 4) cancer cells secrete chemicals that absorb strongly in the mid-infrared region and it is these chemicals that contribute to the spectral changes. Examples 1–5 demonstrate the use of single-cell FT-IR microspectroscopy and the acquisition of spectra from single cells in a dried cervical cell sample to obtain data, subsequently processed by PCA and/or PLS. The processed data is used to construct distribution profiles for the spectra of phenotypically differentiated cells. The distribution profiles have a clearly demonstrable diagnostic utility and allow distinction between normal, normal-dysplastic, dysplastic and malignant cells.

Example 1 illustrates the use of single-cell infrared microspectroscopy in conjunction with principal component analysis (PCA) to detect malignant and premalignant conditions in cervical cells. Example 2 demonstrates the construction of a reference set of IR spectra derived from cytologically normal cells which exhibit distinct spectral patterns (i.e, Pattern I and Pattern II). Example 3 demonstrates the construction of a reference set of IR spectra derived from cytologically normal cells exhibiting Pattern I spectra and cytologically dysplastic cells exhibiting Pattern II spectra. Example 4 illustrates a reference set composed of spectra from cytologically normal cells exhibiting Pattern I spectra and cytologically malignant cells exhibiting Pattern II spectra. Example 5 provides a reference set of IR spectra derived from cytologically normal cells with Pattern II spectra and cytologically malignant cells exhibiting Pattern II spectra. In examples 1–5, inclusive, the reference set was compared to FT-IR spectra from cervical smears. The comparison was made using PLS and/or PCR.

Examples 6–8 demonstrate that there exist clearly distinguishable IR spectroscopic differences between cytologically normal cells in a cervical smear diagnosed as "normal" and cytologically normal cells in a cervical smear diagnosed as "cancer" or "dysplasia." In each of these examples, a reference set is assembled from IR spectra of individual cells. Example 6, illustrates a reference set obtained from IR spectra of cytologically normal cells exhibiting Pattern I spectra and cytologically normal cells that were obtained from smears diagnosed as malignant which exhibited Pattern I spectra. Example 7 demonstrates a reference set composed of IR spectra from normal cells exhibiting Pattern II spectra and cytologically normal cells that were obtained from smears diagnosed as malignant exhibiting Pattern II spectra. Example 8 illustrates a reference set obtained from IR spectra of cytologically normal cells exhibiting Pattern II spectra and cytologically normal cells that were obtained from smears diagnosed as dysplasia which exhibited Pattern II spectra.

Example 1

This example illustrates the use of single cell infrared spectroscopy for the detection of malignant and premalignant conditions in cells.

To address some of these issues, the present invention provides a novel method for the acquisition of spectra from cervical scrapings on a cell by cell basis.

1.1 Materials and Methods

Cells were fixed on a custom made ZnS (Cleartran) microscope slide and examined unstained under a Bio-Rad FT-IR UMA-500 microscope linked to a FTS 165 spectrometer. The aperture was adjusted to the size of individual cells and 500 spectra were co-added at a resolution of 8 cm$^{-1}$. Spectra were analyzed in the mid-IR range (950–3000 cm$^{-1}$). Zinc sulfide was chosen as the matrix for the support of the cells for three reasons. It provided a clear support for viewing the cells under a conventional microscope and an IR microscope. Second, the material was resistant to a number of chemicals including the stains used in Pap smears. Third, the material was well suited for the acquisition of spectra in the IR regions of interest.

(a) Preprocessing of Cervical Specimens

Cervical scrapings were collected by the standard brushing procedure. Exfoliated cells from each brush were gently shaken in vials which contained preservative solution (Preserv Cyt, CYTYC Corporation, Marlborough, Mass.). The preservative solution maintained the integrity of the exfoliated cells during transport and storage, and also served to lyse the red blood cells in the cervical scrapings. Vials containing the exfoliated cells were then treated with a CYTYC THIN PREP PROCESSOR®. The processor filtered out the mucus and non-diagnostic debris, and spread the cells in a uniform layer on the ZnS slides. In this manner, it is possible to selectively remove the majority of interfering materials from cervical scraping and obtain a uniform layer of cells while preserving the diagnostically important features of the cells. Infrared microspectroscopy was performed on unstained exfoliated cells which were recorded for their position by a cellfinder. A cellfinder is a microscope slide with a numbered grid. In practice, the cellfinder overlays the cell sample slide providing a numbered grid over the cell sample. Locations on the cell sample can be reconstructed using the grid and its numbering system. Thereafter the slides were stained by the Papanicolaou stain, and were cytologically examined. The results of spectroscopy were then correlated with the cytological findings.

1.2 Results

Figure 2:
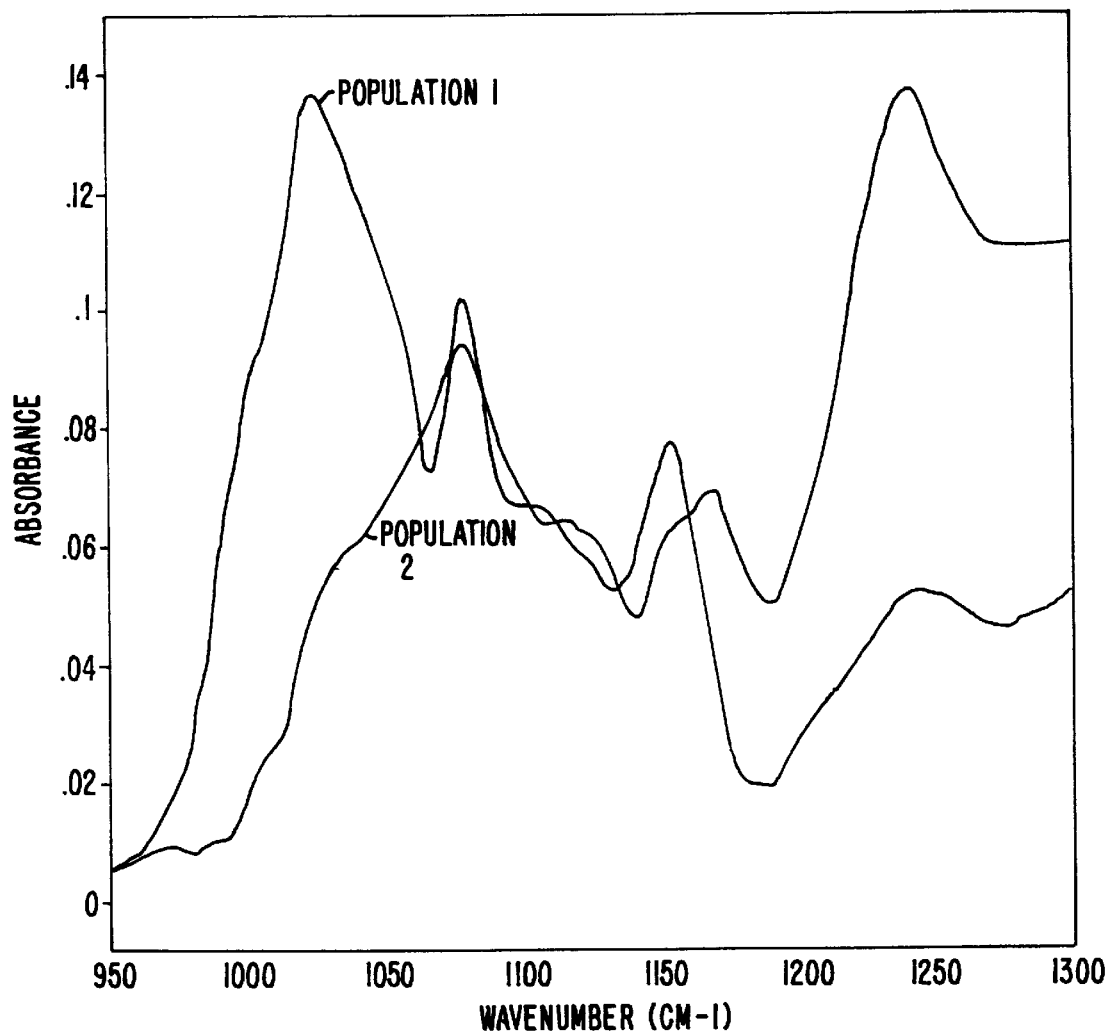
FIG. 2 shows the mid-infrared spectrum (from 950 cm$^{-1}$–1300 cm$^{-1}$) of two populations of squamous epithelial cells.

In the normal cervical scrapings four types of morphologically distinguishable cells were studied. These cells included the mature squamous epithelial cells, the intermediate squamous epithelial cells, parabasal cells and endocervical cells. Two different spectra were typically observed for the normal squamous epithelial cells. One spectrum appeared identical to the spectra for the normal cervical scrapings (FIG. 1), and the other appeared with a significantly diminished band at 1025 cmr$^1$. FIG. 2 shows the spectra of the two squamous cells. Squamous cells that had the typical spectrum of normal cells are referred to as Population 1, and those that lacked the 1025 cm$^{-1}$ band characteristic for glycogen are referred to as Population 2.

Figure 3:
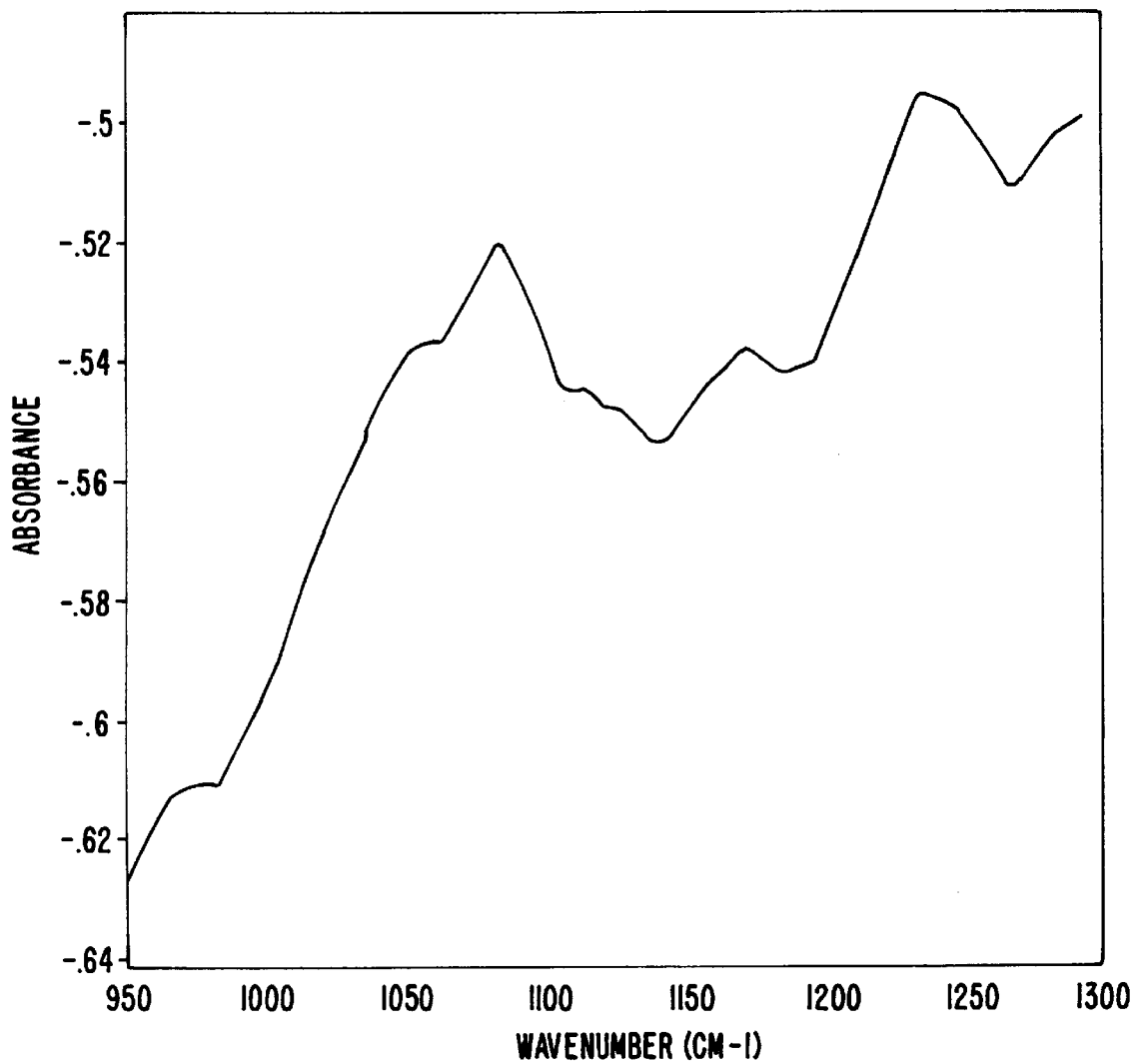
FIG. 3 shows the mid-infrared spectrum (from 950 cm$^{-1}$–1300 cm$^{-1}$) of a malignant cervical scraping.
Figure 4:
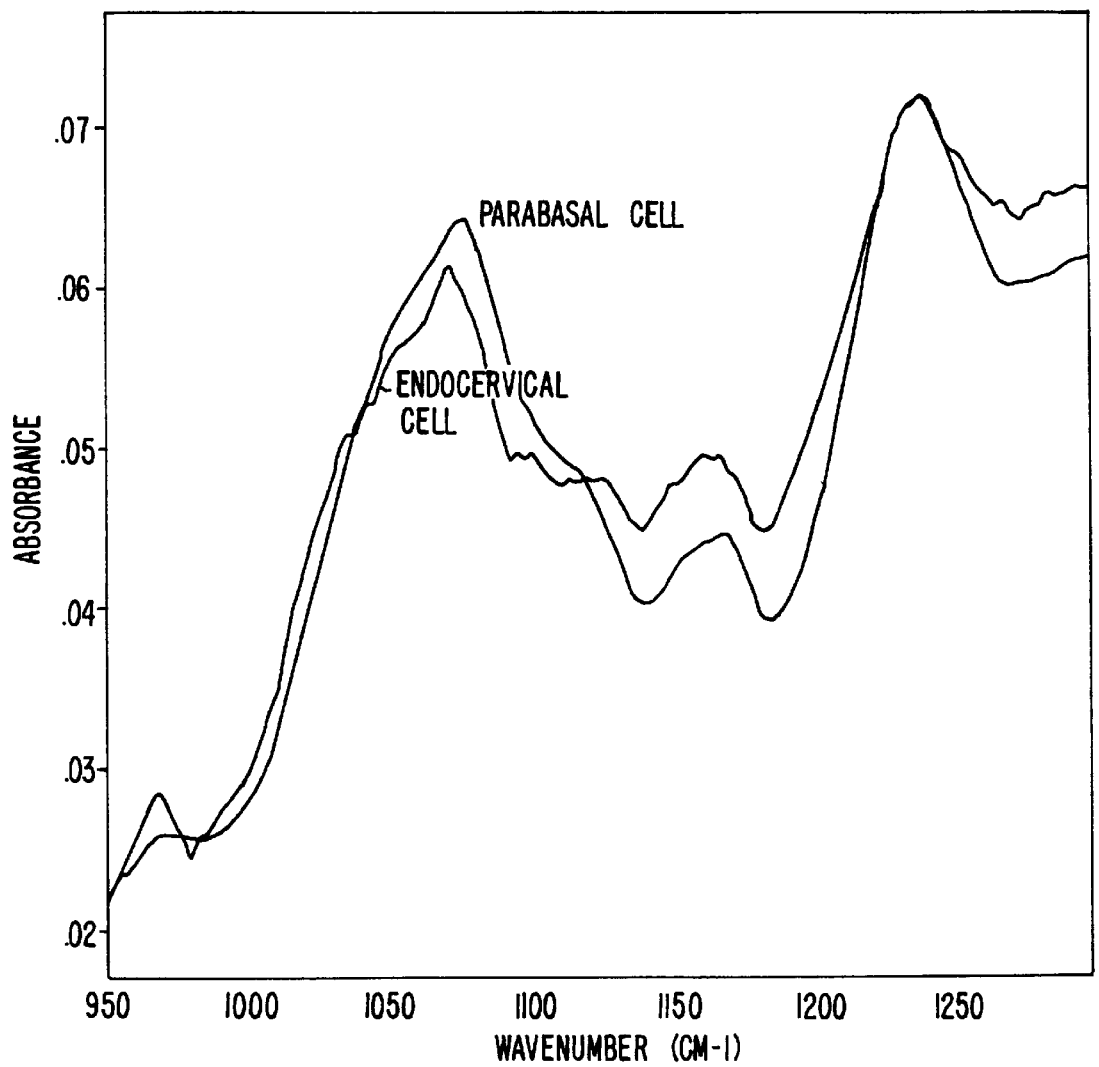
FIG. 4 shows a comparison of the mid-infrared spectra (from 950 cm$^{-1}$–1300 cm$^{-1}$) from parabasal cells and endocervical cells.

The parabasal cells which are normally found in abundance in the cervical scrapings of menopausal patients with estrogen deficiency (e.g. a condition referred to as atrophic) exhibited spectra resembling the spectrum observed in malignant scrapings (FIG. 3, see also Wong, et al., *Proc. Natl. Acad. Sci. USA* 87:8140–8145 (1991)). While the spectra of endocervical cells also exhibited a diminished peak at 1025 cm$^{-1}$, a strong band at the 1076 cm$^{-1}$ region was also observed. FIG. 4 provides a comparison of the spectra of parabasal cells and endocervical cells.

Figure 5:
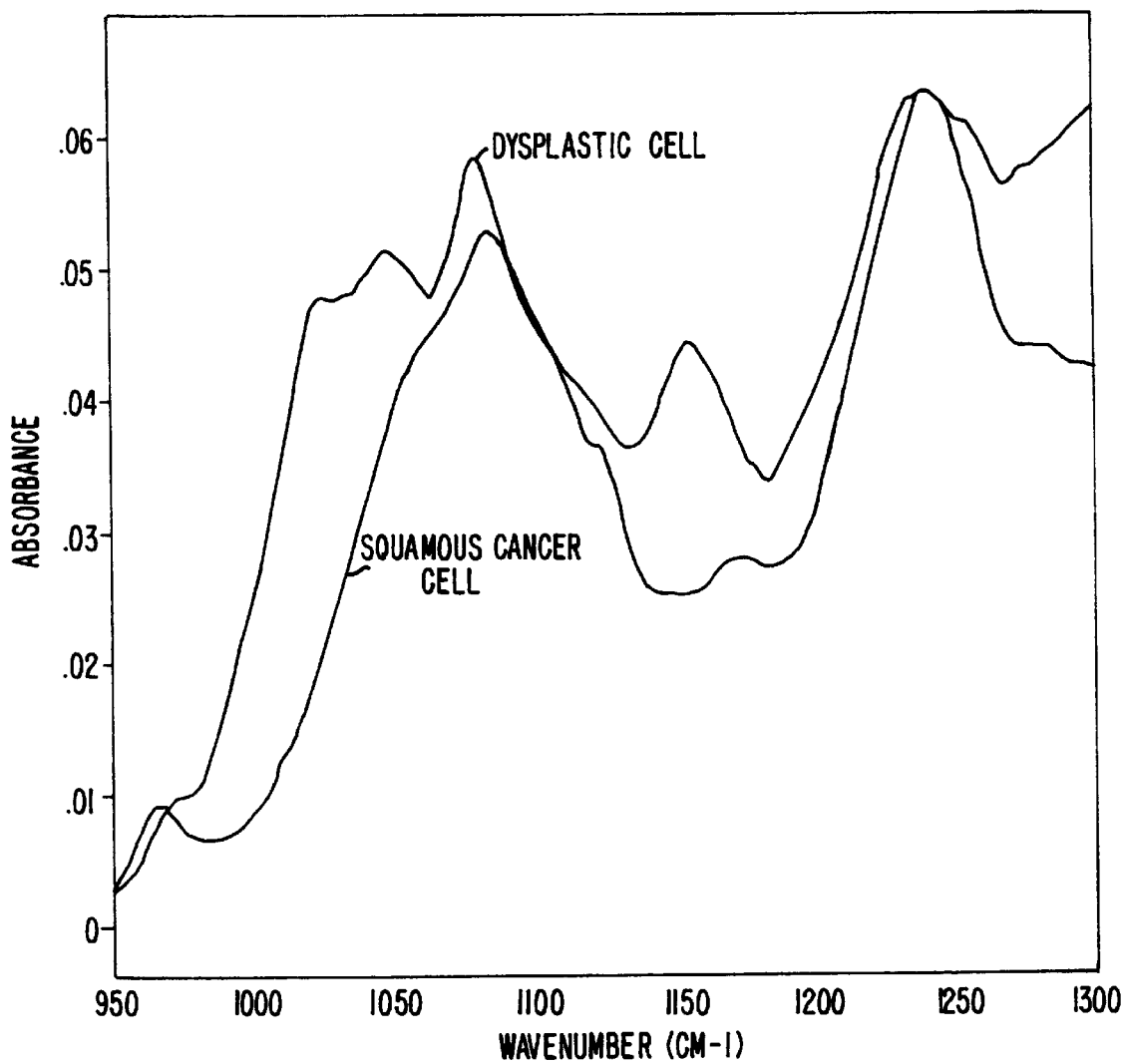
FIG. 5 shows a comparison of the mid-infrared spectra (from 950 cm$^{1}$–1300 cm$^{-1}$) from a dysplastic cell and a squamous cancer cell.

The examination of malignant cells from patients with adenocarcinoma and squamous carcinoma of the cervix confirmed the spectral features reported by Wong, et al., ibid. All the malignant cells exhibited: 1) a prominent band at 970 cm$^{-1}$; and 2) a shift in the 1082 cm$^{-1}$ band to 1086 cm$^{-1}$. The loss in the band at 1025 cm$^{-1}$ was one of the main spectral features of the cancer cells. Microspectroscopic studies also showed that some cells diagnosed cytologically as dysplastic (CIN III) exhibited spectra intermediate in appearance between those of normal and malignant cells. FIG. 5 shows IR spectra from a malignant cell and a dysplastic cell with CIN III characteristics.

Although not wishing to be bound by any particular theory, a current working hypothesis for the mechanism which underlies the experimentally detected spectral changes is outlined below. It is currently thought that, upon undergoing an alteration from the normal phenotype to a disease or pre-disease phenotype, the cervical cell populations undergo a shift in the number of cells which exhibit spectra corresponding to Pattern I, Pattern II or a pattern intermediate between Pattern I and Pattern II. This shift is detectible in the absorption data derived from the cervical cell samples and can constitute the basis for distinguishing between the different cell types in a cervical cell sample.

The following examples will illustrate how single cell infrared spectroscopy based on the distribution of predicted scores generated by PLS or PCR can be used to distinguish normal cervical smears from smears with dysplasia and cancer.

Example 2

Example 2 shows the construction of a reference set of IR spectra derived from diagnostically normal cells which exhibit distinct spectral patterns (Pattern I, Pattern II).

2.1 Materials and Methods (a) Preprocessing of Cervical Scrapings

Cervical scrapings were collected and preserved as described in Example 1.

(b) Preparation and Classification of Cervical Smears

Two separate smears were prepared from each cell suspension with a CYTYC THIN PREP PROCESSOR® (CYTYC Corporation, Marlborough, Mass.). One smear was evaluated by conventional Papanicolaou staining, and the other by infrared microspectroscopy. On the basis of Pap evaluation, smears were classified in one of four diagnostic categories as follows: 1) the smears which were obtained from women with no present or past cervical disease, and which exhibited no morphological abnormality were labeled "normal"; 2) the smears which were acquired from patients with a history of dysplasia, and exhibited no morphological abnormality were labeled "normal-dysplasia"; 3) the smears which exhibited morphological changes associated with neoplasia, but showed no evidence of cancer were labeled "dysplasia"; and 4) those which displayed evidence of carcinoma in situ or cancer were labeled "malignant".

After diagnosing and classifying all specimens, 16 smears were selected for spectroscopic study. This selection was performed at random with the stipulation that within each diagnostic category four smears were to be selected. Of these samples, four smears were classified as "normal", four as "normal-dysplasia", four as "dysplasia", and four as "malignant".

(c) Infrared Spectroscopy

Cervical cells fixed on ZnS (Cleartran) microscope slides were examined unstained under a Bio-Rad FT-IR UMA-500 microscope linked to a Bio-Rad FTS 165 spectrometer. The selection of cells for spectroscopy was performed at random and, since the morphological features of the unstained cells were barely detectable under low magnification, no cytological features influenced the selection process. The aperture was adjusted to the size of individual cells, and 700 scans were co-added at a resolution of 8 cm$^{-1}$. A single-beam spectrum of Cleartran window was used for a background reference with each spectrum. Unless otherwise indicated, from every smear approximately 100 spectra-each corresponding to a single cell-were collected.

(d) Chemometric Analysis

The PLS plus® computer program from Galactic Industries (Salem, N.H., USA) was used to evaluate the spectra of individual cells by different multivariate techniques such as Partial Least Squares (PLS) and Principle Component Regression (PCR). All spectra were normalized to have the minimum and the maximum absorbance set at 0.0 and 1.0, respectively. Normalization was confined to the region between 1000 cm$^{-1}$ and 3000 cm$^{-1}$, because most of the spectral changes between the normal and abnormal cervical specimens appeared in this region. Unless otherwise indicated, two spectral regions were utilized in the PCR or the PLS analysis. These regions included the frequency zones between 1200 cm$^{-1}$ to 1000 cm$^{-1}$, and 3000 cm$^{-1}$ to 2800 cm$^{-1}$. The calculation of F ratios, and the assignment of probability values to different spectra based on F ratio results, were performed by the method of Haaland and Thomas (*Anal. Chem.*, 60:1193 (1988); and *Anal. Chem.*, 60:1202 (1988)). All spectra with F-ratios corresponding to probability values greater than 0.99 were flagged out as outlier samples (PLSplus™ Add-on Application Software manual for GRAMS/386™ page 61, Galactic Industries Corporation, Salem, N.H.). Ranks for different reference spectra were selected on the basis of the Prediction Residual Error Sum of Squares (PRESS), and comparison of the PRESS values with all ranks prior to the PRESS value at the minimum. The first rank that fell below the cut off probability level of 0.75 in the F test of significance was selected as the optimal rank for the analysis (PLSplus™ Add-on Application Software manual for GRAMS/386™ pages 55–56, Galactic Industries Corporation, Salem, N.H.).

(e) Analysis of Spectra by Visual Inspection

Inspection of the spectra of individual cells revealed that there existed primarily two spectroscopic patterns. Pattern I was characterized by a prominent band peaking at around 1025 cm$^{-1}$, and additional discrete bands peaking at around 1080 cm$^{-1}$, 1160 cm$^{-1}$, and a broad peak at around 1250 cm$^{-1}$. Pattern II was characterized by a significant reduction in the amplitude of the 1025 cm$^{-1}$ band, which had now lost its peak, and broadening of the 1080 cm$^{-1}$, and 1160 cm$^{-1}$ bands; the 1250 cm$^{-1}$ band maintained the features of the corresponding band in Pattern I (See FIG. 6). All other spectra appeared either atypical or as a hybrid of "Pattern I" and the "Pattern II" spectra.

(f) Reference Spectra

While a combination of references can be used in conjunction with PCR, and/or PLS to differentiate between normal and abnormal cervical smears, because of space limitations, the examples here will be confined to only four sets of reference spectra that were employed in the analysis.

2.2 Reference Set I

Reference Set I was comprised of two spectral patterns, each derived exclusively from a cytologically "normal" smear. One reference included a subset of normal cells that exhibited the Pattern I spectra, and the other reference was from a subset of normal cells that yielded the Pattern II spectra. Once the reference set was prepared, the spectra exhibiting Pattern I were assigned a dummy variable of 0, and those exhibiting Pattern II were assigned a dummy variable of 1. A rank of 3 was selected for discrimination purposes. This rank was the first rank that fell below the cut off probability level of 0.75 in the F test of significance.

2.3 Results

Figure 7:
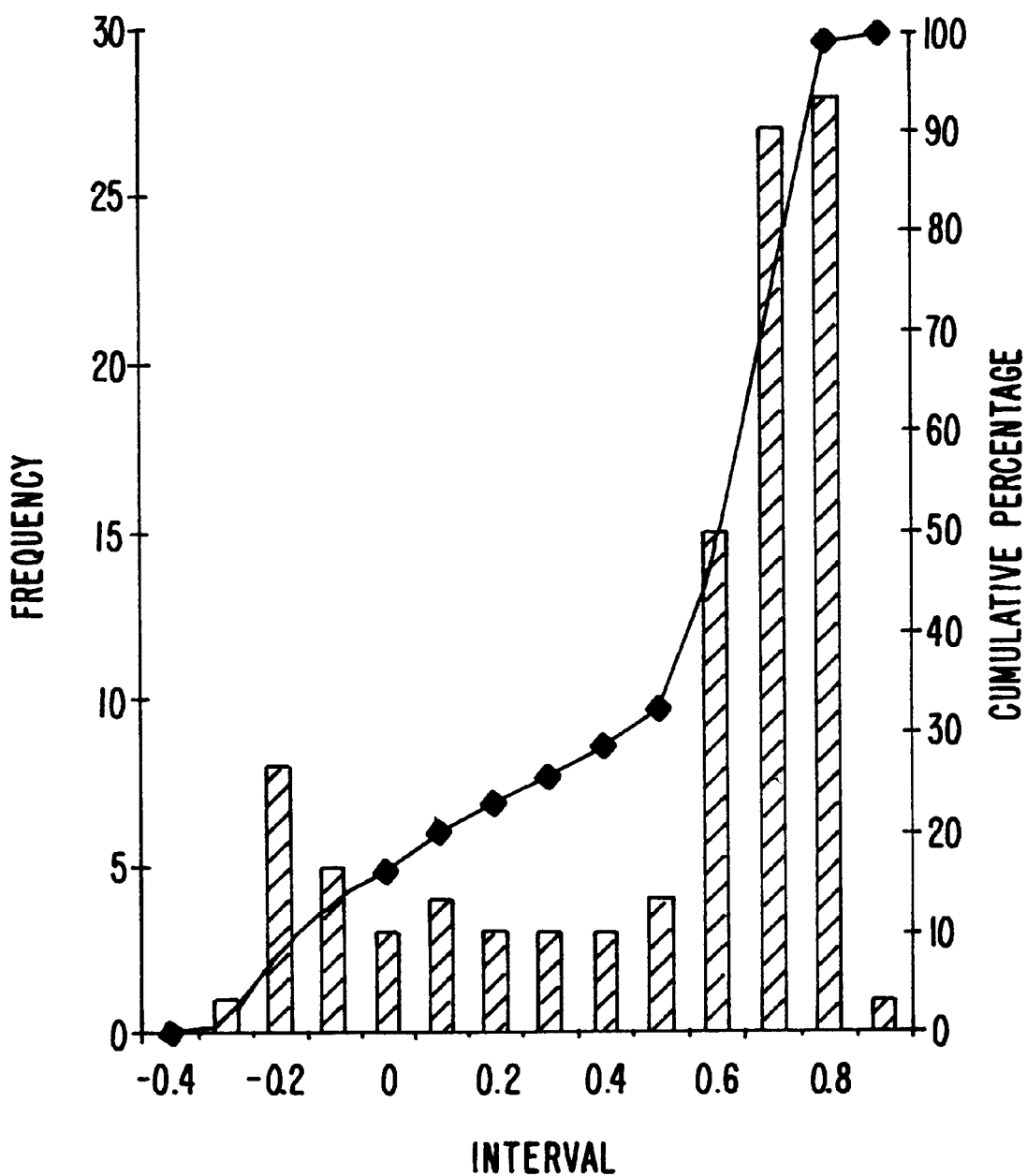
FIG. 7 shows a histogram representation of a set of predicted scores in a normal smear.

The spectra from different smears were stored in separate files and were evaluated by PLS and PCR. PLS and PCR generated a predicted score for each spectrum. The predicted scores from each smear were then sorted, and a histogram of their frequency distribution was constructed. Tables 1 and 2 show a series of such data. These data sets represent the distribution of the PLS predicted scores in each smear. FIG. 7 is a histogram representation of one of the data sets in Table 1. The x axis shows equally divided intervals, while a left and a right y axis indicate the frequency and the cumulative percentage of the predicted scores within the x intervals, respectively.

Figure 8:
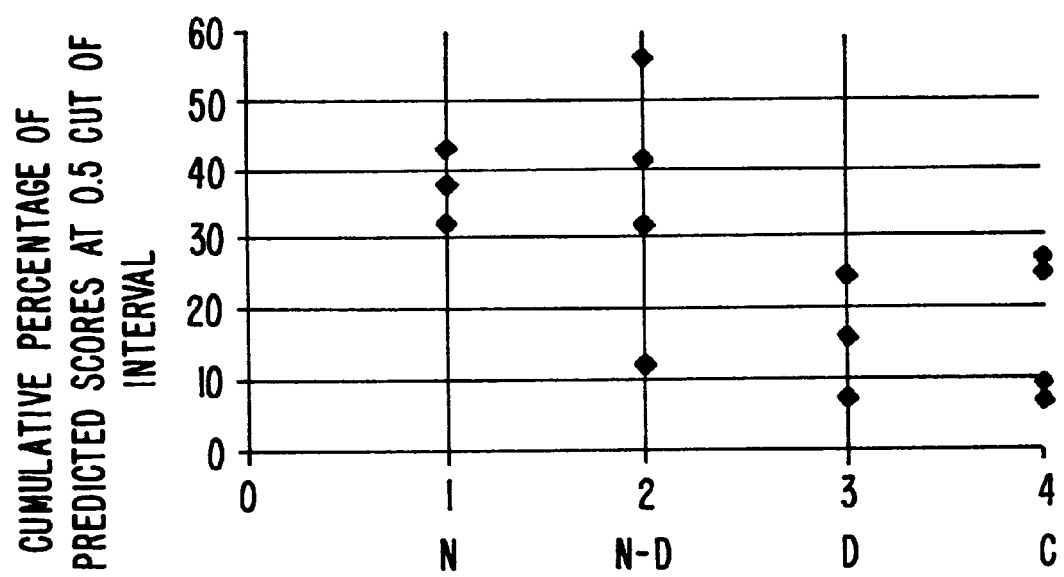
FIG. 8 summarizes the cumulative percentage of predicted scores at the 0.5 cut off interval based on histogram computations from all smears with reference set I.

FIG. 8 summarizes the histogram computations at the 0.5 cut off interval based on the cumulative percentages of the predicted scores for all smears. The data clearly shows that at the 0.5 cut off interval there exists no overlap between the percent cumulative predicted scores from "normal" smears, and smears that were diagnosed with "dysplasia" or cancer. However, some overlap does exist between the percent cumulative predicted scores of the dysplasia and cancer smears with smears that were classified "normal-dysplasia". Included in FIG. 8 one also finds the mean, and the standard error of the mean for the predicted scores (i.e., in the four groups of smears) in each diagnostic category.

Statistical evaluation of the data clearly demonstrates significant differences in the mean score of normal specimens versus the smears with dysplasia and cancer. One explanation for this difference might be that compared to abnormal smears (e.g., dysplasia and cancer), normal smears appear to have more cells exhibiting the Pattern I spectra, and fewer cells that yield the Pattern II spectra. This speculation is based on the observation that the mean predicted score of normal smears is closest to 0, whereas in abnormal specimens it is closest to 1 (e.g., recalling that the reference spectra associated with Patterns I and II were assigned dummy variable values of 0 and 1, respectively). With the progression of cervical disease from normal→normal dysplasia→dysplasia→cancer, one also notices an increase in the magnitude of spectral changes. For example, whereas the normal cervical smears yielded a mean predicted score of 0.443, the specimens with "normal dysplasia", dysplasia and cancer yielded increasing average scores of 0.499, 0.621 and 0.643, respectively. Analysis of the spectra by PCR revealed the same findings (data not shown).

TABLE 1

DISTRIBUTION OF PREDICTED SCORES IN CERVICAL SMEARS DIAGNOSED NORMAL OR NORMAL DYSPLASIA USING CALIBRATION SET I

| | No. 1 | | No. 2 | | No. 3 | | No. 4 | |
|---|---|---|---|---|---|---|---|---|
| | Frequency | Cum % | Frequency | Cum % | Frequency | Cum % | Frequency | Cum % |
| Normal Specimen Interval | | | | | | | | |
| −0.3 | 1 | 0.95 | 0 | 0.00 | 0 | 0 | 0 | 0 |
| −0.2 | 8 | 8.57 | 2 | 2.04 | 0 | 0 | 7 | 7 |
| −0.1 | 5 | 13.33 | 8 | 8.16 | 3 | 3 | 8 | 15 |
| 0 | 3 | 18.19 | 3 | 11.22 | 15 | 18 | 5 | 20 |
| 0.1 | 4 | 20.00 | 0 | 11.22 | 8 | 26 | 5 | 25 |
| 0.2 | 3 | 22.88 | 5 | 18.33 | 5 | 31 | 3 | 28 |
| 0.3 | 3 | 25.71 | 8 | 22.45 | 3 | 34 | 7 | 35 |
| 0.4 | 3 | 28.51 | 5 | 27.55 | 8 | 40 | 3 | 38 |
| 0.5 | 4 | 32.38 | 10 | 31.76 | 3 | 43 | 5 | 43 |
| 0.6 | 15 | 48.87 | 19 | 57.14 | 8 | 51 | 12 | 55 |
| 0.7 | 27 | 72.38 | 23 | 80.81 | 21 | 72 | 22 | 77 |
| 0.8 | 28 | 99.05 | 19 | 100.00 | 27 | 99 | 23 | 100 |
| 0.9 | 1 | 100.00 | | | 1 | 100 | | |
| Total | 105 | | 98 | | 100 | | 100 | |
| Normal-Dysplasia Specimen Interval | | | | | | | | |
| −0.1 | 4 | 4.08 | 8 | 8.12 | 2 | 2.04 | 5 | 5.26 |
| 0 | 1 | 5.10 | 10 | 16.33 | 7 | 9.18 | 15 | 21.05 |
| 0.1 | 0 | 5.10 | 8 | 24.49 | 4 | 13.27 | 7 | 28.42 |
| 0.2 | 4 | 9.18 | 10 | 34.89 | 3 | 16.33 | 4 | 32.83 |
| 0.3 | 0 | 9.18 | 8 | 42.88 | 4 | 20.41 | 3 | 35.79 |
| 0.4 | 2 | 11.22 | 8 | 51.02 | 8 | 26.53 | 1 | 36.84 |
| 0.5 | 1 | 12.24 | 5 | 58.12 | 5 | 31.63 | 4 | 41.05 |
| 0.6 | 3 | 15.31 | 8 | 64.29 | 11 | 42.88 | 3 | 44.21 |
| 0.7 | 17 | 32.85 | 15 | 79.59 | 19 | 62.24 | 13 | 57.89 |
| 0.8 | 85 | 98.98 | 20 | 100.00 | 37 | 100.00 | 36 | 95.79 |
| 0.9 | 1 | 100.00 | | | | | 4 | 100.00 |
| Total | 98 | | 98 | | 98 | | 95 | |

TABLE 2

DISTRIBUTION OF PREDICTED SCORES IN MALIGNANT AND DYSPLASTIC CERVICAL SMEARS USING CALIBRATION SET I

| | No. 1 | | No. 2 | | No. 3 | | No. 4 | |
|---|---|---|---|---|---|---|---|---|
| | Frequency | Cum % | Frequency | Cum % | Frequency | Cum % | Frequency | Cum % |
| Cancer Specimen Interval | | | | | | | | |
| −0.1 | 0 | 0.00 | 0 | 0 | 0 | 0.00 | 0 | 0 |
| 0 | 1 | 1.01 | 0 | 0 | 0 | 0.00 | 0 | 0 |
| 0.1 | 2 | 3.03 | 3 | 3 | 1 | 1.00 | 0 | 0 |
| 0.2 | 2 | 5.05 | 2 | 5 | 2 | 3.23 | 1 | 1 |
| 0.3 | 9 | 14.14 | 4 | 9 | 3 | 6.45 | 0 | 1 |
| 0.4 | 8 | 20.20 | 7 | 16 | 1 | 7.53 | 1 | 1 |
| 0.5 | 7 | 27.27 | 9 | 25 | 2 | 9.88 | 8 | 7 |
| 0.6 | 10 | 37.37 | 8 | 33 | 4 | 13.88 | 2 | 9 |
| 0.7 | 21 | 58.59 | 23 | 56 | 20 | 35.48 | 20 | 29 |

TABLE 2-continued

DISTRIBUTION OF PREDICTED SCORES IN MALIGNANT AND DYSPLASTIC CERVICAL SMEARS USING CALIBRATION SET I

|  | No. 1 | | No. 2 | | No. 3 | | No. 4 | |
|---|---|---|---|---|---|---|---|---|
|  | Frequency | Cum % | Frequency | Cum % | Frequency | Cum % | Frequency | Cum % |
| 0.8 | 41 | 100.00 | 42 | 98 | 56 | 95.70 | 85 | 94 |
| 0.0 |  |  | 2 | 100 | 4 | 100.00 | 8 | 100 |
| Total Dysplasia Specimen Interval | 99 |  | 100 |  | 93 |  | 100 |  |
| -0.2 | 0 | 0.00 | 0 | 0.00 | 0 | 0.00 | 0 | 0.00 |
| -0.1 | 1 | 0.88 | 1 | 1.28 | 3 | 2.88 | 5 | 0.00 |
| 0 | 0 | 0.98 | 0 | 1.25 | 8 | 8.57 | 1 | 1.01 |
| 0.1 | 0 | 0.88 | 2 | 3.75 | 3 | 11.43 | 0 | 1.01 |
| 0.2 | 0 | 0.88 | 2 | 8.25 | 4 | 15.24 | 0 | 1.01 |
| 0.3 | 2 | 2.94 | 3 | 10.00 | 3 | 18.10 | 1 | 2.02 |
| 0.4 | 4 | 6.88 | 2 | 12.50 | 2 | 20.00 | 2 | 4.04 |
| 0.5 | 1 | 7.84 | 3 | 18.28 | 5 | 24.78 | 3 | 7.07 |
| 0.6 | 11 | 18.83 | 8 | 23.75 | 20 | 43.81 | 3 | 10.10 |
| 0.7 | 37 | 54.90 | 26 | 88.28 | 34 | 76.19 | 28 | 38.38 |
| 0.8 | 48 | 100.00 | 33 | 97.80 | 28 | 100.00 | 81 | 100.00 |
| 0.9 |  |  | 2 | 100.00 | 0 |  |  |  |
| Total | 102 |  | 80 |  | 105 |  | 99 |  |

Example 3

Example 3 demonstrates the construction of a reference set of IR spectra derived from normal cells exhibiting Pattern I spectra and dysplastic cells exhibiting Pattern II spectra.

3.1 Materials and Methods

The materials and methods used in Example 3 are substantially the same as those described in Example 2.

3.2 Reference Set II

Reference set II was comprised from two reference spectra. One reference included a subset of cytologically normal single cells that exhibited the Pattern I spectra, and that were derived from smears which were diagnosed "normal". The second reference included a subset of cytologically normal single cells that exhibited the Pattern II spectra, but which were derived from smears that were cytologically classified with "dysplasia". These reference spectra were selected at random and from different normal and dysplasia smears to ensure a thorough representation of the two spectral patterns. The spectra exhibiting Pattern I were assigned a dummy variable of 0, and the spectra exhibiting Pattern II were assigned a dummy variable of 1. Only one spectral region was utilized in the PCR or the PLS analysis. This frequency region included the zone between 1200 $cm^{-1}$ to 1000 $cm^{-1}$. For discrimination purposes, a rank of 6 was selected for the analysis.

3.3 Results

Figure 9:
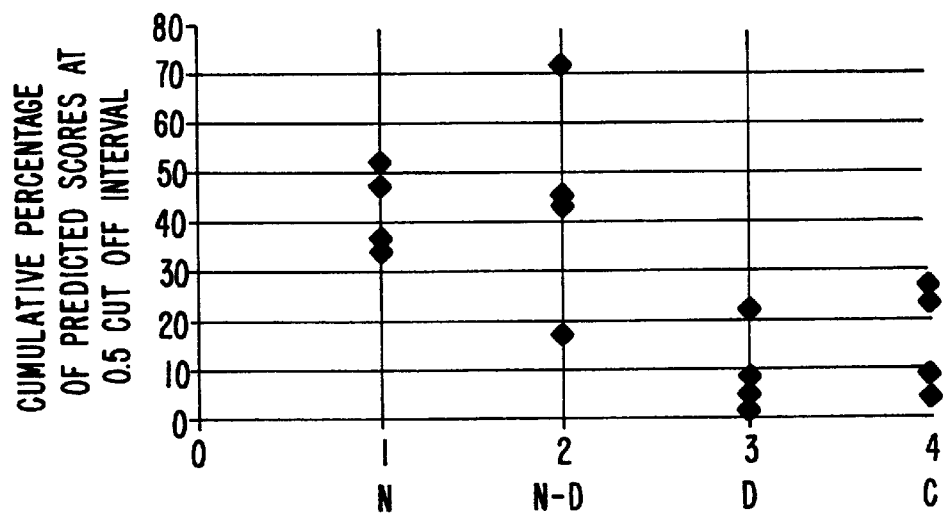
FIG. 9 summarizes the cumulative percentage of predicted scores at the 0.5 cut off interval based on histogram computations from all smears with reference set II.

Tables 3 through 6 show a series of discrete data based on computations made by PLS using reference set II as the reference spectra. Each data set represents one smear, and summarizes the distribution of predicted scores within that smear. Table 7 furnishes the mean and the standard deviation of the predicted scores that were computed for each smear. Statistical analysis of the data indicates a significant difference in the mean of the predicted scores of normal specimens relative to the specimens with dysplasia or cancer. A comparison of PLS results using reference set II versus reference set I also revealed a wider spread in the means of the predicted scores of the normal cervical smears relative to the smears with dysplasia or cancer. While there are several possible explanations for this difference, we speculate that this change is brought about by subtle differences between the Pattern II spectra of cells in normal specimens, and of the Pattern II spectra of cells in the specimens with dysplasia. The progression of normal cells to dysplasia might be biochemically induced, and IR spectroscopy could be providing a window onto the results or origins of these biochemical changes. Additionally, as in the previous reference, the results here indicate that normal cervical smears have a higher percentage of cells with the Pattern I spectra compared to the dysplasia smears where the cells with Pattern II spectra predominate. The closeness to 0 in the mean of the predicted scores of normal smears, and to 1 of that of the abnormal smears supports this conclusion (e.g., the reference spectra associated with Patterns I and II were assigned dummy variable values of 0 and 1, respectively). Finally, if one examines the cumulative predicted scores of the histogram results for all smears at the 0.5 cut off interval, it becomes evident that reference set II, like reference set I, clearly demarcates the normal smears from the smears with dysplasia and cancer (see FIG. 9).

The findings using PCR analysis were similar (data not shown).

TABLE 3

DISTRIBUTION OF PREDICTED SCORES IN MALIGNANT CERVICAL SMEARS
USING CALIBRATION SET II

| Interval | Sample No. 1 | | Sample No. 2 | | Sample No. 3 | | Sample No. 4 | |
|---|---|---|---|---|---|---|---|---|
| | Frequency | Cum % | Frequency | Cum % | Frequency | Cum % | Frequency | Cum % |
| −0.1 | 0 | 0 | 0 | 0 | 1 | 1.086957 | 0 | 0 |
| 0 | 0 | 0 | 0 | 0 | 0 | 1.086957 | 0 | 0 |
| 0.1 | 6 | 8.185567 | 3 | 3.030303 | 1 | 2.173913 | 0 | 0 |
| 0.2 | 3 | 9.278351 | 2 | 5.050505 | 1 | 3.26087 | 0 | 0 |
| 0.3 | 9 | 18.5567 | 8 | 13.13131 | 0 | 3.26087 | 1 | 1.06383 |
| 0.4 | 4 | 22.68041 | 4 | 17.17172 | 1 | 4.347626 | 0 | 1.06383 |
| 0.5 | 4 | 26.80412 | 6 | 23.23232 | 4 | 8.695652 | 3 | 4.255319 |
| 0.6 | 6 | 32.98969 | 9 | 32.32323 | 1 | 9.782609 | 3 | 7.446809 |
| 0.7 | 16 | 49.48454 | 12 | 44.44444 | 6 | 16.30435 | 3 | 10.6383 |
| 0.8 | 30 | 80.41237 | 36 | 80.80808 | 14 | 31.52174 | 15 | 26.59574 |
| 0.9 | 12 | 92.78351 | 12 | 92.92929 | 31 | 65.21739 | 24 | 52.12766 |
| 1 | 1 | 93.81443 | 5 | 97.9798 | 17 | 83.69565 | 29 | 82.97672 |
| 1.1 | 4 | 97.93614 | 0 | 97.9798 | 10 | 94.56522 | 11 | 94.68085 |
| 1.2 | 1 | 98.96907 | 2 | 100 | 2 | 96.73913 | 5 | 100 |
| 1.3 | 1 | 100 | 0 | 100 | 1 | 97.82609 | 0 | 100 |
| 1.4 | 0 | 100 | 0 | 100 | 0 | 97.82609 | 0 | 100 |
| 1.5 | 0 | 100 | 0 | 100 | 1 | 98.91304 | 0 | 100 |
| 1.6 | 0 | 100 | 0 | 100 | 1 | 100 | 0 | 100 |
| Total | 97 | | 99 | | 92 | | 94 | |

TABLE 4

DISTRIBUTION OF PREDICTED SCORES IN DYSPLASTIC CERVICAL SMEARS
USING CALIBRATION SET II

| Interval | Sample No. 1 | | Sample No. 2 | | Sample No. 3 | | Sample No. 4 | |
|---|---|---|---|---|---|---|---|---|
| | Frequency | Cum % | Frequency | Cum % | Frequency | Cum % | Frequency | Cum % |
| −0.2 | 0 | 0 | 0 | 0 | 0 | 0 | 1 | 1.111111 |
| −0.1 | 0 | 0 | 0 | 0 | 1 | 0.952381 | 0 | 1.111111 |
| 0 | 0 | 0 | 0 | 0 | 1 | 1.904762 | 0 | 1.111111 |
| 0.1 | 1 | 1 | 0 | 0 | 2 | 3.809524 | 0 | 1.111111 |
| 0.2 | 1 | 2 | 0 | 0 | 6 | 9.52381 | 0 | 1.111111 |
| 0.3 | 0 | 2 | 1 | 1.298701 | 5 | 14.28571 | 0 | 1.111111 |
| 0.4 | 0 | 2 | 2 | 3.896104 | 3 | 17.14286 | 2 | 3.333333 |
| 0.5 | 1 | 3 | 3 | 7.792208 | 5 | 21.90476 | 1 | 4.444444 |
| 0.6 | 4 | 7 | 7 | 16.88312 | 2 | 28.57143 | 2 | 6.666667 |
| 0.7 | 13 | 20 | 7 | 25.97403 | 14 | 41.90476 | 4 | 11.11111 |
| 0.8 | 41 | 61 | 23 | 55.84416 | 22 | 62.85714 | 10 | 22.22222 |
| 0.9 | 34 | 95 | 19 | 80.51948 | 28 | 89.52381 | 23 | 47.77778 |
| 1 | 4 | 99 | 9 | 92.20779 | 4 | 93.33333 | 26 | 76.66667 |
| 1.1 | 1 | 100 | 4 | 97.4026 | 3 | 96.19048 | 15 | 93.33333 |
| 1.2 | 0 | 100 | 1 | 98.7013 | 1 | 97.14286 | 4 | 97.77778 |
| 1.3 | 0 | 100 | 1 | 98.7013 | 2 | 99.04762 | 2 | 100 |
| 1.4 | 0 | 100 | 1 | 98.7013 | 0 | 99.04762 | 0 | 100 |
| 1.5 | 0 | 100 | 1 | 98.7013 | 0 | 99.04762 | 0 | 100 |
| 1.6 | 0 | 100 | 1 | 98.7013 | 1 | 100 | 0 | 100 |
| 1.7 | 0 | 100 | 1 | 98.7013 | 0 | 100 | 0 | 100 |
| 1.8 | 0 | 100 | 1 | 98.7013 | 0 | 100 | 0 | 100 |
| 1.9 | 0 | 100 | 1 | 98.7013 | 0 | 100 | 0 | 100 |
| 2 | 0 | 100 | 0 | 98.7013 | 0 | 100 | 0 | 100 |
| 2.1 | 0 | 100 | 1 | 100 | 0 | 100 | 0 | 100 |
| Total | 100 | | 77 | | 105 | | 90 | |

TABLE 5

DISTRIBUTION OF PREDICTED SCORES IN NORMAL CERVICAL SMEARS USING CALIBRATION SET II

| | Sample No. 1 | | Sample No. 2 | | Sample No. 3 | | Sample No. 4 | |
|---|---|---|---|---|---|---|---|---|
| Interval | Frequency | Cum % | Frequency | Cum % | Frequency | Cum % | Frequency | Cum % |
| −0.3 | 3 | 2.941176 | 4 | 4.123711 | 1 | 1.010101 | 1 | 1.041667 |
| −0.2 | 2 | 4.901961 | 1 | 5.154839 | 3 | 4.040404 | 2 | 3.125 |
| −0.1 | 6 | 10.78431 | 5 | 10.30928 | 6 | 10.10101 | 6 | 9.375 |
| 0 | 9 | 19.60784 | 1 | 11.34021 | 7 | 17.17172 | 5 | 14.58333 |
| 0.1 | 3 | 22.54902 | 5 | 16.49485 | 9 | 26.26263 | 3 | 17.70833 |
| 0.2 | 3 | 25.4902 | 5 | 21.64948 | 8 | 34.34343 | 5 | 22.91667 |
| 0.3 | 1 | 26.47059 | 6 | 27.83505 | 10 | 44.44444 | 9 | 32.29167 |
| 0.4 | 2 | 28.43137 | 3 | 30.92784 | 3 | 47.47475 | 5 | 37.5 |
| 0.5 | 5 | 33.33333 | 5 | 36.08247 | 4 | 51.51515 | 9 | 48.875 |
| 0.6 | 5 | 38.23529 | 26 | 62.8866 | 5 | 56.56566 | 8 | 55.20833 |
| 0.7 | 22 | 59.80392 | 22 | 85.56701 | 9 | 65.65657 | 22 | 78.125 |
| 0.8 | 20 | 79.41176 | 7 | 92.78351 | 26 | 91.91919 | 17 | 95.83333 |
| 0.9 | 18 | 97.05882 | 4 | 96.90722 | 8 | 97.9798 | 2 | 97.91667 |
| 1 | 3 | 100 | 3 | 100 | 2 | 100 | 2 | 100 |
| Total | 102 | | 97 | | 99 | | 96 | |

TABLE 6

DISTRIBUTION OF PREDICTED SCORES IN NORMAL AND DYSPLASTIC CERVICAL SMEARS USING CALIBRATION SET II

| | Sample No. 1 | | Sample No. 2 | | Sample No. 3 | | Sample No. 4 | |
|---|---|---|---|---|---|---|---|---|
| Interval | Frequency | Cum % | Frequency | Cum % | Frequency | Cum % | Frequency | Cum % |
| −0.6 | 0 | 0 | 1 | 1.030928 | 0 | 0 | 0 | 0 |
| ..0.5 | 0 | 0 | 1 | 2.061856 | 0 | 0 | 0 | 0 |
| ..1.4 | 0 | 0 | 1 | 3.092784 | 1 | 1.041667 | 0 | 0 |
| ..0.3 | 0 | 0 | 2 | 5.154639 | 2 | 3.125 | 1 | 1.086957 |
| ..0.2 | 2 | 2.105263 | 4 | 9.278351 | 3 | 6.25 | 1 | 2.173913 |
| ..0.1 | 2 | 4.210528 | 9 | 18.5567 | 4 | 10.41687 | 7 | 9.782609 |
| 0 | 2 | 6.315789 | 9 | 27.83505 | 2 | 12.5 | 8 | 18.47820 |
| 0.1 | 3 | 9.472684 | 12 | 40.20619 | 8 | 20.83333 | 6 | 25 |
| 0.2 | 1 | 10.52832 | 6 | 46.39175 | 7 | 28.125 | 4 | 29.34783 |
| 0.3 | 0 | 10.52632 | 9 | 55.6701 | 8 | 36.45833 | 6 | 35.86957 |
| 0.4 | 2 | 12.63158 | 11 | 67.01031 | 2 | 38.54167 | 1 | 38.95852 |
| 0.5 | 4 | 18.84211 | 4 | 71.13402 | 6 | 44.79167 | 5 | 42.3913 |
| 0.6 | 5 | 22.10526 | 8 | 79.38144 | 13 | 58.3333 | 1 | 43.47826 |
| 0.7 | 15 | 37.89474 | 11 | 90.72165 | 16 | 75 | 16 | 60.86957 |
| 0.8 | 38 | 77.89474 | 5 | 95.87629 | 11 | 86.45833 | 21 | 83.69565 |
| 0.9 | 14 | 92.63158 | 3 | 98.96907 | 9 | 95.83333 | 13 | 97.82609 |
| 1 | 5 | 97.89474 | 1 | 100 | 3 | 98.95833 | 2 | 100 |
| 1.1 | 2 | 100 | 0 | 100 | 1 | 100 | 0 | 100 |
| Total | 95 | | 97 | | 96 | | 92 | |

TABLE 7

STATISTICAL ANALYSIS OF PREDICTED SCORES GENERATED BY CALIBRATION SET II

| Sample Numbers | # of Spectra With Acceptable F-ratio | Average of Predicted Scores | Std. Deviation of Predicted Scores STDEV | Std. Error of the Mean SEM | Ave. of Means | STDEV of Means | SEM |
|---|---|---|---|---|---|---|---|
| | | NORMAL CERVICAL SAMPLES | | | | | |
| 1 | 102 | 0.5032 | 0.3742 | 0.037051 | 0.445558 | 0.042731 | 0.021366 |
| 2 | 97 | 0.44248 | 0.31467 | 0.03195 | | | |
| 3 | 99 | 0.40015 | 0.3567 | 0.036051 | | | |
| 4 | 96 | 0.4384 | 0.31748 | 0.032403 | | | |
| | | CERVICAL SMEARS WITH DYSPLASTIC | | | | | |
| 1 | 100 | 0.75953 | 0.1262 | 0.01262 | 0.772033 | 0.08356 | 0.04178 |
| 2 | 77 | 0.779 | 0.22067 | 0.025148 | | | |
| 3 | 105 | 0.673 | 0.282 | 0.02752 | | | |
| 4 | 90 | 0.6766 | 0.2024 | 0.021335 | | | |

TABLE 7-continued

STATISTICAL ANALYSIS OF PREDICTED SCORES GENERATED BY CALIBRATION SET II
CERVICAL SMEARS WITH CANCER

| 1 | 97 | 0.6178   | 0.26742 | 0.027152 | 0.741433 | 0.130744 | 0.065372 |
|---|----|----------|---------|----------|----------|----------|----------|
| 2 | 99 | 0.64143  | 0.23425 | 0.023543 |          |          |          |
| 3 | 92 | 0.831    | 0.233   | 0.024292 |          |          |          |
| 4 | 94 | 0.8755   | 0.15946 | 0.016447 |          |          |          |

CERVICAL SMEARS WITH NORMAL DYSPLASTIC

| 1 | 95 | 0.6463   | 0.26262  | 0.028996 | 0.444768 | 0.168378 | 0.084189 |
|---|----|----------|----------|----------|----------|----------|----------|
| 2 | 97 | 0.234746 | 0.35617  | 0.036164 |          |          |          |
| 3 | 96 | 0.438908 | 0.355538 | 0.036287 |          |          |          |
| 4 | 92 | 0.481121 | 0.361554 | 0.037695 |          |          |          |

Example 4

Example 4 illustrates a reference set composed of spectra from normal cells exhibiting Pattern I spectra and malignant cells with Pattern II spectra.

4.1 Materials and Methods

The materials and methods used in this example are substantially the same as those used in Example 2.

4.2 Reference Set III

Reference set III was comprised of two reference spectra. One reference spectrum included a subset of cytologically normal single cells that exhibited the Pattern I spectra, and that were derived from the cytologically diagnosed smears labeled "normal". The second reference spectrum included a subset of cytologically normal single cells which exhibited the Pattern II spectra, and which were derived from smears which were cytologically diagnosed as "malignant". These reference spectra were selected at random; each was from different normal and malignant smears, to ensure a thorough representation of the two spectral patterns. The spectra exhibiting Pattern I were assigned a dummy variable of 0, and the spectra exhibiting Pattern II were assigned a dummy variable of 1. For final analysis, a rank of 6 was selected for discrimination purposes.

4.3 Results

Figure 10:
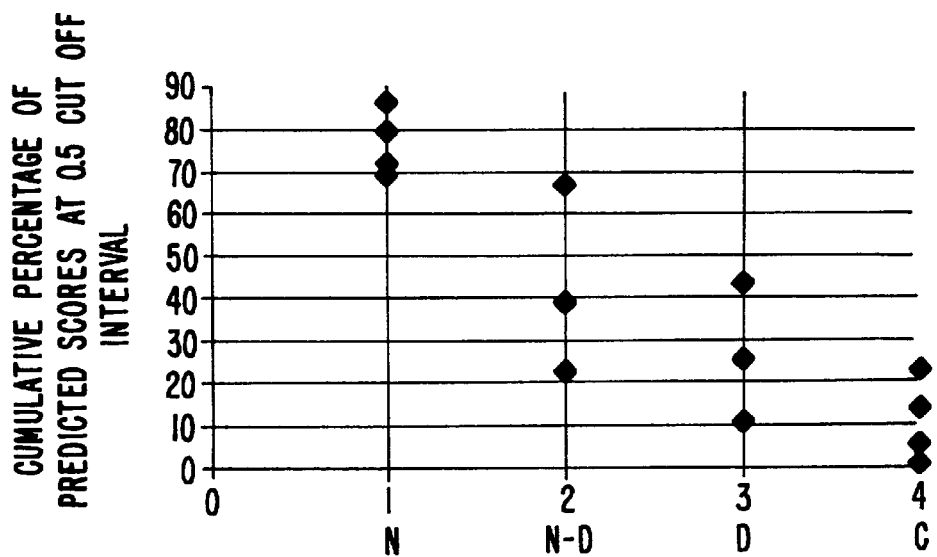
FIG. 10 summarizes the cumulative percentage of predicted scores at the 0.5 cut off interval based on histogram computations from all smears with reference set III.

Reference set m was employed in PLS analysis to compute predicted scores for all spectra. These predicted scores were then converted into a series of discrete data in a manner identical to the entries which were made earlier (See Tables 1, 2, and 4). FIG. 10 summarizes the histogram computations at the 0.5 cut off interval based on the cumulative percentages of the predicted scores for all smears. The data clearly shows that at the 0.5 cut off interval there exists no overlap between the percent cumulative predicted scores of "normal" smears, and the smears which were diagnosed with "dysplasia" and cancer. Also provided in FIG. 10 are the means and the standard deviations of the predicted scores for the four groups of smears. Close scrutiny of the data indicates that the choice of reference affects the spread in the mean of the predicted scores of the various categories of smears. More importantly, the extent in the spread seems to be directly related to type of spectra in the reference set, and the degree of abnormality of the cells from which the spectra were derived. Therefore, in using the spectra of cells from cancer smears, it was not surprising that the greatest spread in the mean of predicted scores was observed with data which was generated by reference set III. Likewise, it was not unusual to discover that the spread in the means of the predicted scores for all groups of smears was greatest for data which was generated by reference set II versus reference set I. A possible explanation for this observation is that the difference in the means of the predicted scores is related primarily to the Pattern II spectra, and is brought about by the gradual conversion of normal cells to cancer, with dysplasia cells acting as an intermediary stage during this transformation process. Lastly, it is important to note, that in the transition from normalcy to malignancy there appears also a gradual shift in the percentage of cells exhibiting the Pattern I spectral features. For example, whereas the highest percentage of cells with Pattern I spectra are found in "normal" smears (FIG. 6), there is a lower percentage of these cells in "dysplasia" smears, and far lower in the "malignant" smears.

Example 5

Example 5 illustrates a reference set of IR spectra derived from cytologically normal single cells in smears diagnosed as normal with Pattern II spectra and cytologically normal cells in smears diagnosed as malignant exhibiting Pattern II spectra.

5.1 Materials and Methods

The materials and methods used in this example are substantially the same as those used in Example 2.

5.2 Reference Set IV

In an attempt to explore the variation in the Pattern II spectra of normal and cancer smears, a reference consisting of only the Pattern II spectra was created. Those spectra which were derived from cytologically "normal" smears were assigned a dummy variable of 0, and those which were selected from cytologically "malignant" smears were assigned a dummy variable of 1. The rank of 6 was selected for discrimination purposes.

5.3 Results

Figure 11:
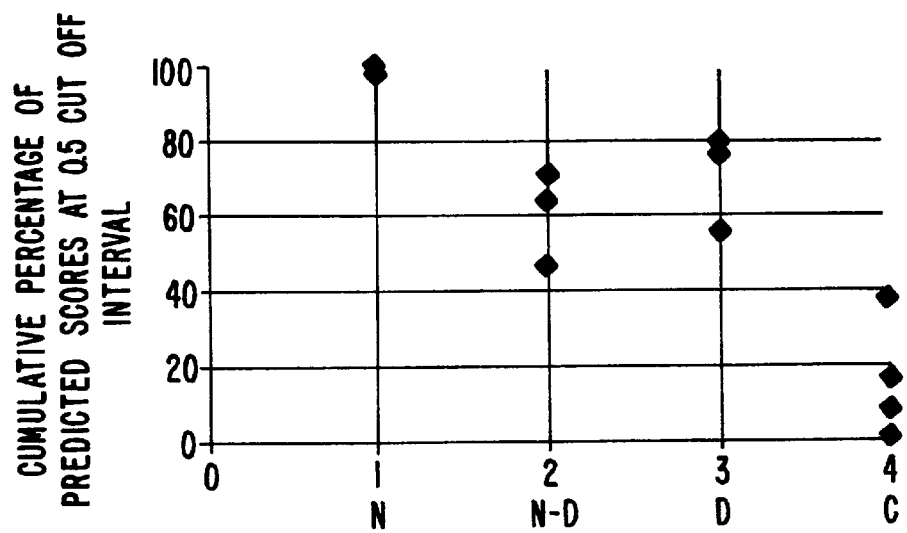
FIG. 11 summarizes the cumulative percentage of predicted scores at the 0.5 cut off interval based on histogram computations from all smears with reference set IV.

Discrimination between the different categories of smear was most dramatic with this reference spectra. FIG. 11 summarizes the histogram computations at the 0.5 cut off interval for all smears. With the spectra of over 97% of the cells in the "normal" smears having a predicted score at or below the 0.5 cut off interval, PLS analysis using reference set IV clearly demarcated the "normal" smears from all other smears. Also, as was intuitively anticipated, the highest percentage of spectra with predicted scores >0.5 were found in the group of smears which were labeled "malignant".

Most interesting was the percent difference at the 0.5 cut off interval in the predicted scores of the "normal" smears, and the cervical smears which were labeled "normal-dysplasia". For example, whereas 29% to 45% of the cells in the "normal dysplasia" smears had predictive scores greater than 0.5, no more than 2% of the cells in the normal smears were above the 0.5 cut off interval.

The following examples illustrate how single cell infrared spectroscopy based on the distribution of predicted scores generated by PLS or PCR can be used to distinguish normal cervical smears from smears with dysplasia and cancer.

Example 6

6.1 Materials and Methods

The materials and methods used in Example 6 are substantially the same as those described in Example 2. Differences include slight changes in the spectroscopic method, the classification of the cells and the assignment of IR spectroscopic absorption bands.

(a) IR Microspectroscopy For single-cell IR spectroscopy, the aperture was adjusted to the size of individual cells, and 700 scans were co-added at a resolution of 8 cm$^{-1}$. Unless otherwise indicated, from every smear approximately 100 spectra each corresponding to a different individual cell were collected.

(b) Preparation and Classification of Cervical Smears

Two separate smears were prepared from each cell suspension with a CYTYC THIN PREP PROCESSOR® (CYTYC Corporation, Malborough, Mass.). One smear was evaluated by conventional Papanicalou staining, and the other by infrared microspectroscopy. On the basis of Pap evaluation, smears were classified in one of three diagnostic categories as follows: The smears which were obtained from women with no present or past cervical disease, and which exhibited no morphological evidence of disease were labeled "normal". The smears which exhibited changes associated with neoplasia, but showed no evidence of cancer were labeled "dysplasia", and those which displayed evidence of carcinoma in situ or cancer were labeled "malignant". After diagnosing and classifying all specimens, 12 smears were selected for spectroscopic study. Of these samples, four smears corresponded to cervical scrapings which were by Pap diagnosis classified as "normal", four to samples identified as "dysplasia", and four to "malignant".

(c) Assignment of Bands

According to previous studies the spectrum of mammalian glycogen is characterized by prominent bands at around 1026 cm$^{-1}$, 1080 cm$^{-1}$ and 1153 cm$^{-1}$ all of which can be readily seen in Pattern I spectra. The symmetric phosphate stretching modes contribute to the bands at 1080 cm$^{-1}$ as well (Wong et al); they have been suggested to originate from the phophodiester groups of nucleic acids. The asymmetric phosphate stretching modes contribute to the band at around 1244 cm$^{-1}$; this band is not seen in the IR spectrum of glycogen.

6.2 Reference Set I

Reference Set I was constructed from two categories of reference spectra with all the spectra exhibiting the typical Pattern I spectral features. Category 1 consisted of only those spectra which were acquired from cytologically normal single cells from Pap smears which were diagnosed as "normal", and with the smears originating from women who had no prior history of cervical disease. Category 2 consisted of spectra of cytologically normal single cells which were obtained from smears diagnosed with "cancer," and with the smears originating from women confirmed to suffer from cervical malignancy. Once the reference set was prepared, the spectra in category 1 were assigned a dummy variable of 0, and those in category 2 were assigned a dummy variable of 1. A rank of 9 was selected for discrimination purposes. The rank of 9 was the first rank which fell below the cut off probability level of 0.75 in the F test of significance.

6.3 Results

Figure 12:
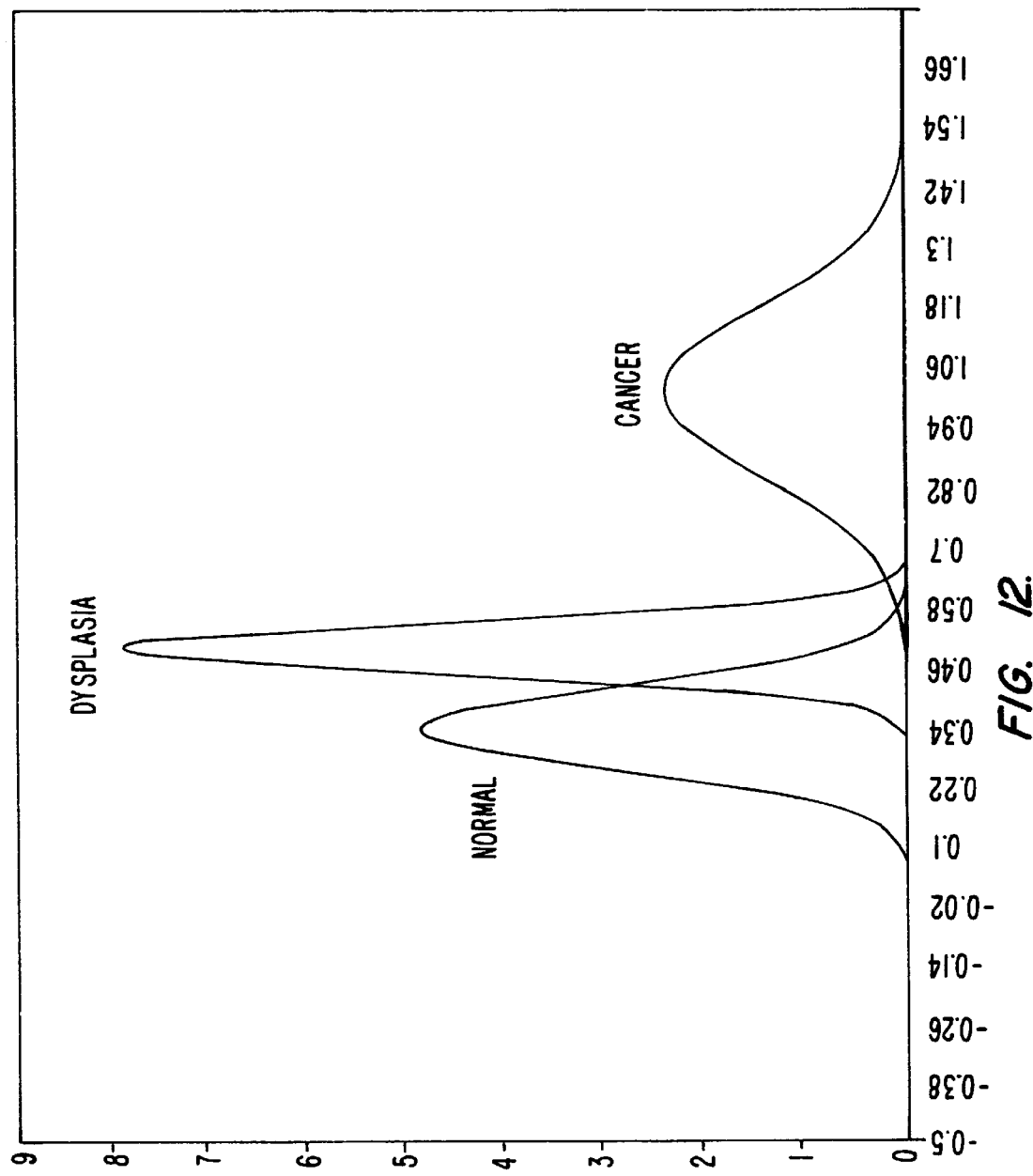
FIG. 12 is a normal distribution curve displaying the means and standard deviations of 4 each of normal, dysplasia and cancer specimens. The curve was constructed using Pattern I spectra of normal cells versus Pattern I of cancer cells.

The spectra from different smears were evaluated by PLS and PCR. PLS and PCR generated a predicted score for each cell that was analyzed. These predicted scores (i.e, excluding the scores of the outlier cells) were then averaged to yield one score for every smear which was analyzed. Table 8 shows a series of discrete data which represent the average score of each of the 12 smears which were evaluated (i.e., 4 normal, 4 dysplasia, and 4 cancer). Mean and standard deviations were then computed based on these scores for each of the diagnostic categories. FIG. 12 shows three normal distribution curves which were generated from these means and standard deviations. The curve on the left represents the distribution of these scores in the normal smears, the curves at the center and at the right represent the same in the dysplasia and cancer smears, respectively.

TABLE 8

| Slides | Normal | Dysplasia | Cancer |
| --- | --- | --- | --- |
| 1 | 0.36219 | 0.41582 | 1.090887 |
| 2 | 0.427498 | 0.489598 | 1.174956 |
| 3 | 0.289767 | 0.524743 | 0.940745 |
| 4 | 0.242362 | 0.51772 | 0.80367 |
| Mean | 0.330454 | 0.48697 | 1.002565 |
| Std. Dev. | 0.081323 | 0.049805 | 0.164216 |

Statistical evaluation of the data clearly demonstrates significant differences in the mean score of normal specimens versus the smears with dysplasia and cancer. One plausible explanation for this difference may be that cells from normal smears have a content of glycogen distinct from the cytologically normal cells in the smears with dysplasia and cancer. This finding is in concordance with the studies of Schiller, W., *Surg. Gynecol. Obstet.,* 56:210 (1933), whereby marked intensity differences in the staining for glycogen were observed in the cervix of normal and abnormal patients.

Analysis of the spectra by PCR revealed the same findings as those detailed above (data not shown).

Example 7

7.1 Materials and Methods

The materials and methods used in Example 7 were substantially the same as those used in Example 6.

7.2 Reference Set II

Reference Set II was constructed from two categories of reference spectra with all the spectra exhibiting the typical Pattern II spectral features. Category 1 consisted of only those spectra which were acquired from cytologically normal single cells from Pap smears which were diagnosed as "normal", and with the smears originating from women who had no prior history of cervical disease. Category 2 consisted of spectra of cytologically normal single cells which were obtained from smears diagnosed with "cancer", and with the smears originating from women which were confirmed to have cervical cancer. As before, the spectra in category 1 were assigned a dummy variable of 0, and the spectra in category II were assigned a dummy variable of 1. A rank of 6 was selected for discrimination purposes. The rank of 6 was the first rank which fell below the cut off probability level of 0.75 in the F test of significance.

7.3 Results

Figure 13:
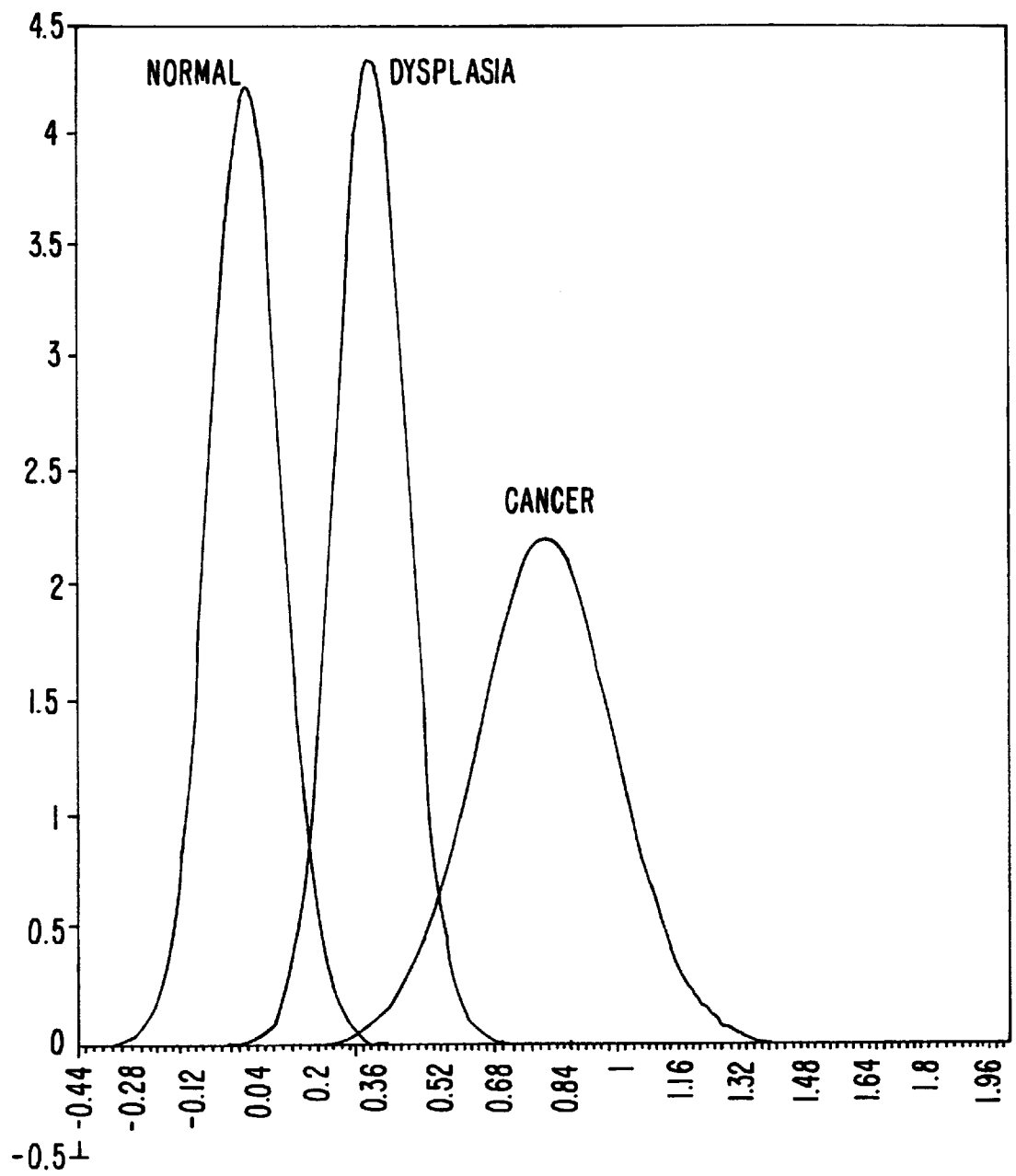
FIG. 13 is a normal distribution curve displaying the means and standard deviations of 4 each of normal, dysplasia and cancer specimens. The curve was constructed using Pattern II spectra of normal cells versus Pattern II of cancer cells.

The spectra from different smears were, once again, evaluated by PLS and PCR. PLS and PCR generated a predicted score for each cell, and these predicted scores (i.e, excluding the scores of the outlier cells) were then averaged to yield one score for every smear which was analyzed. Table 9 shows a series of discrete data which represent the average score of each of the 12 smears which were evaluated (i.e., 4 normal, 4 dysplasia, and 4 cancer). Mean and standard deviations were computed as before for each of the diagnostic categories. FIG. 13 shows three normal distribution curves which were generated from these means and standard deviations. The curve on the left represents the distribution of these scores in the normal smears; the curves at the center and at the right represent the same in the dysplasia and cancer smears, respectively.

TABLE 9

| Slides | Normal | Dysplasia | Cancer |
|---|---|---|---|
| 1 | −0.0027 | 0.318 | 0.557 |
| 2 | −0.102 | 0.213 | 0.745 |
| 3 | 0.127 | 0.349 | 0.847 |
| 4 | −0.0158 | 0.435 | 0.9818 |
| Mean | 0.001625 | 0.32875 | 0.7827 |
| Std. Dev. | 0.09448 | 0.091675 | 0.179013 |

Analysis of the spectra by PCR revealed the same findings as described above (data not shown).

Example 8

8.1 Materials and Methods

The materials and methods used in Example 8 are substantially the same as those used in Example 6.

8.2 Reference Set III

Reference Set m was constructed from two categories of reference spectra with all the spectra exhibiting the typical Pattern II spectral features. Category 1 consisted of only those spectra which were acquired from cytologically normal single cells from Pap smears which were diagnosed as "normal", and with the smears originating from women who had no prior history of cervical disease. Category 2 consisted of spectra of cytologically normal single cells which were obtained from smears diagnosed with "dysplasia", and with the smears originating from women which were confirmed by biopsy to have cervical dysplasia. As before, the spectra in category 1 were assigned a dummy variable of 0, and the spectra in category II were assigned a dummy variable of 1. A rank of 5 was selected for discrimination purposes. The rank of S was the first rank which fell below the cut off probability level of 0.75 in the F test of significance. Table 10 shows a series of discrete data which represent the average score of each of the 12 smears which were evaluated (i.e., 4 normal, 4 dysplasia, and 4 cancer).

TABLE 10

| Slides | Normal | Dysplasia | Cancer |
|---|---|---|---|
| 1 | 0.201779 | 0.787387 | 0.920703 |
| 2 | 0.582902 | 0.701948 | 0.87411 |
| 3 | 0.251409 | 0.671977 | 0.930559 |
| 4 | 0.330684 | 0.711378 | 0.996935 |
| Mean | 0.341694 | 0.718173 | 0.930577 |
| Std. Dev. | 0.169342 | 0.049106 | 0.505627 |

8.3 Results

Figure 14:
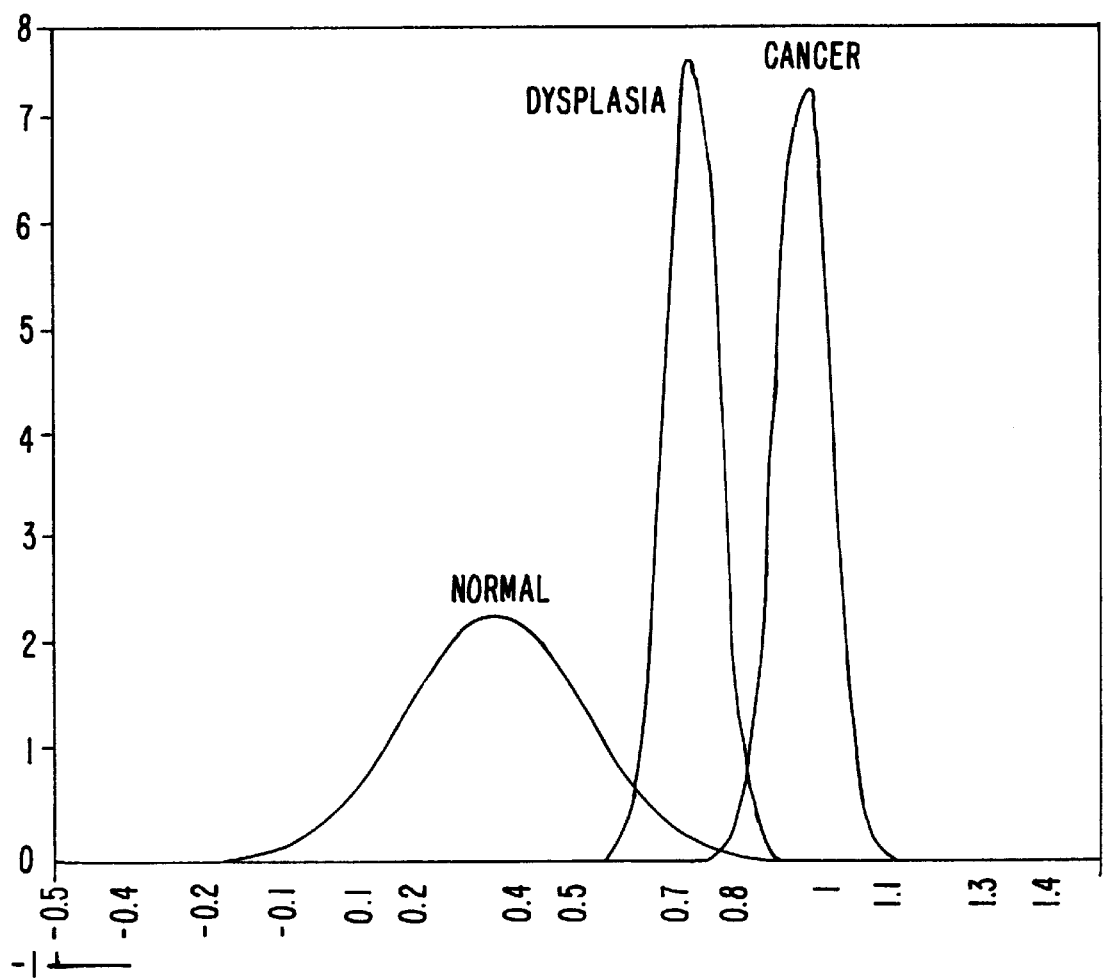
FIG. 14 is a normal distribution curve displaying the means and standard deviations of 4 each of normal, dysplasia and cancer specimens. The curve was constructed using Pattern II spectra of normal cells versus Pattern II spectra of dysplastic cells.
Figure 15:
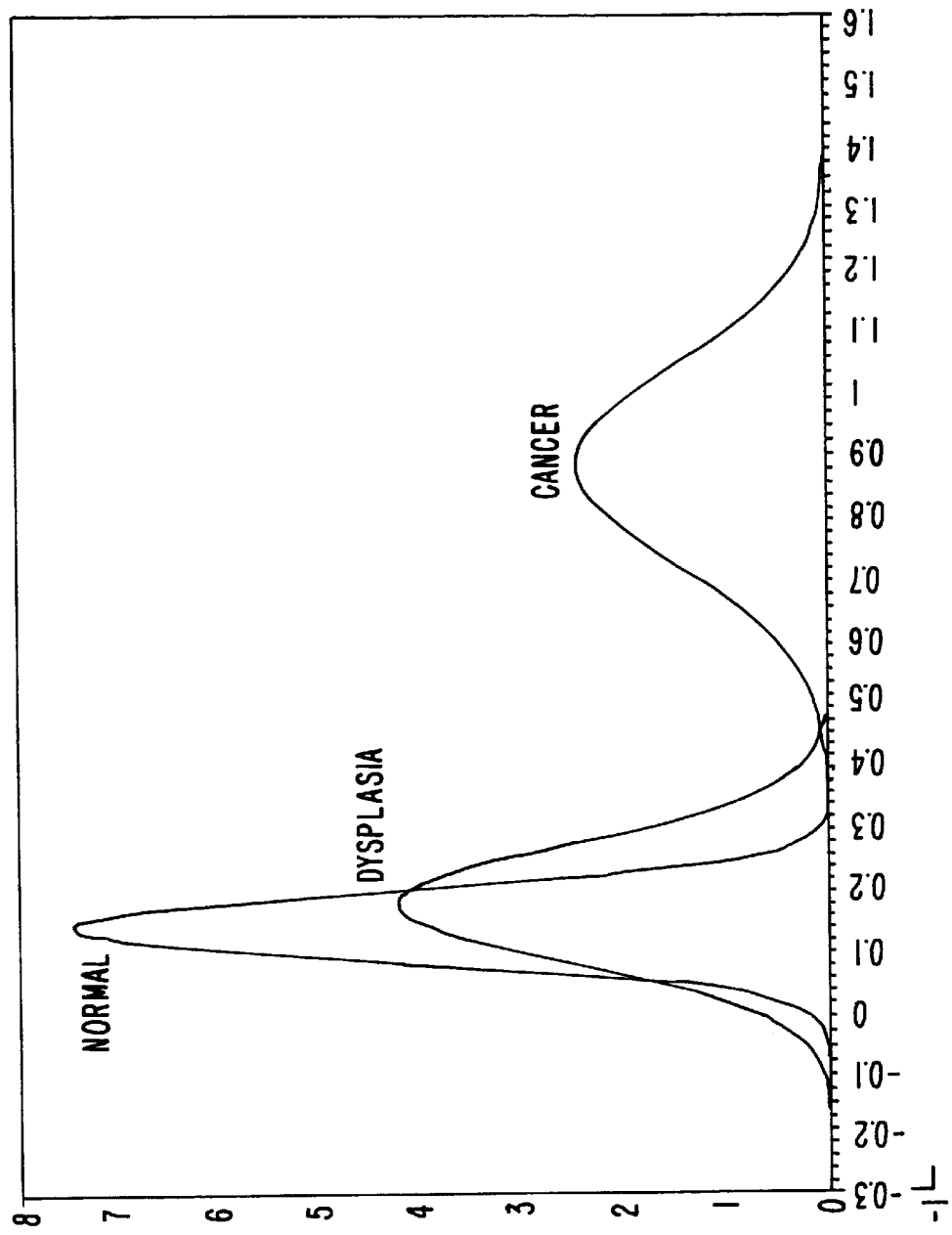
FIG. 15 is a normal distribution curve displaying the means and standard deviations of four each of normal, dysplasia and cancer specimens. The curve was constructed using combined Pattern I and Pattern II spectra of cytologically normal cells from normal smears and combined Pattern I and Pattern II spectra of cytologically normal cells from cancer smears.

Reference set III was employed in PLS analysis to compute predicted scores for all spectra. The predicted scores from each cell were then averaged and analyzed in a manner similar to the examples which were presented earlier (See Reference I and II). FIG. 14 depicts the normal distribution for the three categories of smear; normal, dysplasia and cancer. Once again, the curve at the left represents the distribution of normal smears; and the curves at the center and the right represent spectral data from the dysplasia and cancer smears, respectively.

With the current techniques of cytological analysis (e.g., the Pap smear), it is impossible to distinguish between normal cervical smears which are derived from women with no prior history of dysplasia, and normal cervical smears which are derived from individuals with a past history of such a disease. That IR spectroscopy is distinguishing between these two groups of smears is therefore a vital finding. It is indeed probable that the observed difference in the percentages between the "normal" and the "normal-dysplasia" smears reflects significant chemical changes in the cervical cells which persist long after the dysplastic phenotype has reverted to normal, and that these changes can be detected by IR microspectroscopy. Further, it is not possible to detect differences in cytologically "normal" cells which are present in, and make up the bulk of, cervical smears diagnosed as "cancer." Quite surprisingly, the method of the instant invention provide a means with which to distinguish cytologically "normal" cells which are, in fact, "chemically normal" as well from those cells which are cytologically "normal," but "chemically aberrant." In addition, the IR microspectroscopic methods as practiced herein can not only indicate which women are at risk of cervical cancer, but can also assess the degree of this risk, i.e., low versus high risk for cervical cancer.

The present invention provides substantially novel methods for detecting chemical differences between cell types and for distinguishing between normal and diseased cell samples. While specific examples have been provided, the above description illustrative and not restrictive. Many variations of the disclosed methods will be apparent to those of skill in the art upon review of this specification. The scope of the invention should, therefore, be determined not with the reference to the above description, but instead should be determined with reference to the appended claims along with their full scope of equivalents.

It will be apparent to one of skill in the art that the above described techniques, particularly the processing of spectroscopic data using multivariate analysis, will have application to absorption data acquired by spectroscopic techniques other than infrared spectroscopy. For example, differences in the nuclear magnetic resonance (NMR), raman or ultraviolet (UV) spectra of normal and aberrant cells can be used to characterize cell samples using the methods of the invention. The enumerated spectroscopic techniques are given by way of example and are not intended to limit the scope of the invention to use with infrared spectroscopy.

All publications, patents and patent applications mentioned in this specification are herein incorporated by reference into the specification to the same extent as if each individual publication, patent or patent application was specifically and individually indicated to be incorporated herein by reference.

What is claimed is:

1. A method for detecting chemical differences between a cell sample and a reference cell sample, utilizing single-cell infrared microspectroscopy, said method comprising:
   (a) directing a beam of infrared light through an aperture of approximately single cell size at single cells in a cell sample to produce absorption data for each of said single cells;
   (b) comparing said absorption data for each of said single cells with infrared absorption data acquired from individual cells in at least one reference cell sample to provide comparison data for each of said single cells in said cell sample;
   (c) generating scores for said absorption data using said comparison data;
   (d) creating frequency distribution profiles from said scores; and
   (e) detecting said chemical differences using said frequency distribution profiles.

2. A method in accordance with claim 1, wherein said cell sample and said reference cell sample each comprise cells from human tissue.

3. A method in accordance with claim 2, wherein said cell sample and said reference cell sample are from tissues selected from the group consisting of breast, bladder, male reproductive system, female reproductive system, bone, pancreas, brain, skin, digestive tract and lung tissues.

4. A method in accordance with claim 3, wherein said cell sample and said reference cell sample are from tissues selected from the group consisting of breast, male reproductive system and female reproductive system tissues.

5. A method in accordance with claim 1, wherein said cell sample is dried prior to producing said absorption data in step (a).

6. A method in accordance with claim 1, wherein said cell sample is substantially free of non-diagnostic debris.

7. A method according to claim 6, wherein said cell sample and said reference cell sample are cervical cells.

8. A method in accordance with claim 7, wherein infrared absorption data acquired from the cell sample and infrared absorption data acquired from the reference cell sample are compared at one or more frequency ranges selected from the group consisting of 1200 $cm^{-1}$ to 1000 $cm^{-1}$ and 3000 $cm^{-1}$ to 2800 $cm^{-1}$.

9. A method according to claim 1, wherein said chemical differences are due to a disease state in said cell sample.

10. A method according to claim 9, wherein said disease state is a member selected from the group consisting of diseases caused by pathological agents and diseases caused by genetic anomalies.

11. A method according to claim 9, wherein said disease state is a member selected from the group consisting of cancer, hypertrophy and dysplasia.

12. A method according to claim 1, wherein said chemical differences arise from the treatment of a disease state.

13. A method according to claim 1, wherein step (c) further comprises;
   using multivariate analysis of said comparison data to generate said scores.

14. A method according to claim 1, wherein step (c) further comprises:
   using classical spectroscopic analytical methods to generate said scores.

15. A method according to claim 1, wherein said absorption data is a member selected from the group consisting of smoothed, derivatized and smoothed and derivatized absorption data.

16. A method according to claim 1, wherein the absorption data is a member selected from the group consisting of unsmoothed absorption data, underivatized absorption data and unsmoothed and underivatized absorption data.

17. A method for detecting chemical differences between a cell sample and a reference cell sample utilizing single-cell infrared microspectroscopy, said method comprising:
   (a) directing a beam of infrared light through an aperture of approximately single cell size at single cells in said cell sample to produce absorption data for each of said single cells;
   (b) comparing said absorption data for said single cells with infrared absorption spectra acquired from individual cells in at least one reference cell sample to provide comparison data for said single cells;
   (c) generating scores for said absorption data using said comparison data;
   (d) establishing a mean of said scores for said single cells;
   (e) comparing said mean with a reference distribution curve of scores, to detect said chemical differences in said cell sample.

18. A method in accordance with claim 17, wherein said cell sample and said reference cell sample each comprise cells from human tissue.

19. A method in accordance with claim 18, wherein said cell sample and said reference cell sample are from tissues selected from the group consisting of breast, bladder, male reproductive system, female reproductive system, bone, pancreas, brain, skin, digestive tract and lung tissues.

20. A method according to claim 19, wherein said cell sample and said reference cell sample are cervical cells.

21. A method in accordance with claim 20, wherein infrared absorption data acquired from the cell sample and infrared absorption data acquired from the reference cell sample are compared at one or more frequency ranges selected from the group consisting of 1200 $cm^{-1}$ to 1000 $cm^{-1}$ and 3000 $cm^{-1}$ to 2800 $cm^{-1}$.

22. A method in accordance with claim 17, wherein said cell sample is dried prior to producing said absorption data in step (a).

23. A method in accordance with claim 17, wherein said cell sample is substantially free of non-diagnostic debris.

24. A method according to claim 17, wherein said chemical differences are due to a disease state in said cell sample.

25. A method according to claim 24, wherein said disease state is a member selected from the group consisting of diseases caused by pathological agents and diseases caused by genetic anomalies.

26. A method according to claim 24, wherein said disease state is a member selected from the group consisting of cancer, benign hypertrophy and dysplasia.

27. A method according to claim 17, wherein said chemical differences arise from the treatment of a disease state.

28. A method in accordance with claim 17, wherein step (c) further comprises:

using multivariate analysis of said comparison data to generate said scores.

29. A method in accordance with claim 17, wherein step (c) further comprises:

using classical spectroscopic analytical methods to generate said scores.

30. A method according to claim 17, wherein said absorption data is a member selected from the group consisting of smoothed, derivatized and smoothed and derivatized absorption data.

31. A method according to claim 17, wherein the absorption data is a member selected from the group consisting of unsmoothed absorption data, underivatized absorption data and unsmoothed and underivatized absorption data.

32. A method for detecting chemical differences between a cell sample and a reference cell sample utilizing infrared spectroscopic imaging, said method comprising:

(a) directing a beam of infrared light at a cell sample to produce absorption data, substantially simultaneously, for each of a plurality of single cells in said cell sample;

(b) comparing said absorption data for each of said single cells with a reference set of absorption spectra acquired from individual cells in at least one reference cell sample to provide comparison data for each of said single cells in said cell sample;

(c) generating scores for said absorption data using said comparison data;

(d) creating frequency distribution profiles from said scores; and (e) detecting said chemical differences using said frequency distribution profiles.

33. A method in accordance with claim 32, wherein said cell sample and said reference cell sample are from human tissue.

34. A method in accordance with claim 33, wherein said cell sample and said reference cell sample are from tissues selected from the group consisting of breast, bladder, male reproductive system, female reproductive system, bone, pancreas, brain, skin, digestive tract and lung tissues.

35. A method according to claim 34, wherein said cell sample and said reference cell sample are cervical cells.

36. A method according to claim 33, wherein said chemical differences are due to a disease state in said cell sample.

37. A method according to claim 36, wherein said disease state is a member selected from the group consisting of diseases caused by pathological agents and diseases caused by genetic anomalies.

38. A method according to claim 36, wherein said disease state is a member selected from the group consisting of cancer, benign hypertrophy and dysplasia.

39. A method in accordance with claim 32, wherein said cell sample and said reference cell sample are dried cell samples.

40. A method in accordance with claim 32, wherein said cell sample is substantially free of non-diagnostic debris.

* * * * *